US010314771B2

(12) United States Patent
Dehghan et al.

(10) Patent No.: US 10,314,771 B2
(45) Date of Patent: Jun. 11, 2019

(54) METHODS AND COMPOSITIONS FOR PREVENTING AND TREATING TOOTH EROSION

(71) Applicant: University of Tennessee Research Foundation, Knoxville, TN (US)

(72) Inventors: Mojdeh Dehghan, Germantown, TN (US); Daranee Versluis, Memphis, TN (US); Hassan Almoazen, Bartlett, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 15/833,291

(22) Filed: Dec. 6, 2017

(65) Prior Publication Data

US 2018/0092817 A1    Apr. 5, 2018

Related U.S. Application Data

(63) Continuation-in-part of application No. 15/657,791, filed on Jul. 24, 2017, now abandoned, which is a continuation of application No. 14/771,222, filed as application No. PCT/US2014/019447 on Feb. 28, 2014, now Pat. No. 9,744,108.

(60) Provisional application No. 61/770,863, filed on Feb. 28, 2013.

(51) Int. Cl.
*A61K 8/19* (2006.01)
*A61K 8/20* (2006.01)
*A61K 8/21* (2006.01)
*A61K 8/24* (2006.01)
*A61K 8/34* (2006.01)
*A61K 8/41* (2006.01)
*A61K 8/64* (2006.01)
*A61K 8/81* (2006.01)
*A61K 8/97* (2017.01)
*A61Q 11/00* (2006.01)

(52) U.S. Cl.
CPC .............. *A61K 8/21* (2013.01); *A61K 8/19* (2013.01); *A61K 8/20* (2013.01); *A61K 8/24* (2013.01); *A61K 8/345* (2013.01); *A61K 8/41* (2013.01); *A61K 8/64* (2013.01); *A61K 8/8182* (2013.01); *A61K 8/97* (2013.01); *A61Q 11/00* (2013.01); *A61K 2800/20* (2013.01); *A61K 2800/884* (2013.01)

(58) Field of Classification Search
CPC . A61K 8/24; A61K 8/19; A61K 9/005; A61K 33/10; A61K 31/11
USPC ................................................ 424/439, 440
See application file for complete search history.

(56) References Cited

U.S. PATENT DOCUMENTS

| | | | |
|---|---|---|---|
| 4,080,440 A | 3/1978 | DiGiulio et al. | |
| 4,083,955 A * | 4/1978 | Grabenstetter | A61K 8/19 424/49 |
| 4,367,218 A | 1/1983 | Jacobson | |
| 4,606,912 A | 8/1986 | Rudy et al. | |
| 5,571,502 A | 11/1996 | Winston et al. | |
| 5,738,840 A | 4/1998 | Richter et al. | |
| 5,833,957 A | 11/1998 | Winston et al. | |
| 6,159,448 A | 12/2000 | Winston et al. | |
| 7,638,143 B2 * | 12/2009 | Piene | A61K 9/0007 424/687 |
| 9,044,500 B2 * | 6/2015 | Kawa | A61K 8/73 |
| 9,161,909 B2 * | 10/2015 | Domb | A61K 9/006 |
| 2007/0183984 A1 | 8/2007 | Haas et al. | |
| 2007/0196494 A1 * | 8/2007 | Grenier | A61K 9/0056 424/487 |
| 2007/0249733 A1 | 10/2007 | Bae et al. | |
| 2008/0075675 A1 | 3/2008 | Reynolds et al. | |
| 2012/0301408 A1 | 11/2012 | Baker et al. | |
| 2013/0164311 A1 | 6/2013 | Decarlo et al. | |

FOREIGN PATENT DOCUMENTS

| | | | | |
|---|---|---|---|---|
| FR | 3010635 | * | 3/2015 | ............ A61K 31/79 |
| WO | 2002017868 A1 | | 3/2002 | |
| WO | 2011068813 A1 | | 6/2011 | |
| WO | 2012143220 A1 | | 10/2012 | |

OTHER PUBLICATIONS

Hurlbutt, et al. "Dental Caries: A pH-mediated disease."CDHA Journal—Winter 2010; pp. 9-15.
International Search Report and Written Opinion of the International Searching Authority dated Jun. 6, 2014 of International PCT Application No. PCT/US2014/019447 filed Feb. 28, 2014.
Ruan, Qichao, et al. "An amelogenin-chitosan matrix promotes assembly of an enamel-like layer with a dense interface."Acta biomaterialia 9.7 (Apr. 2013): 7289-7297.
International Search Report and Written Opinion of the International Searching Authority dated Nov. 14, 2014 of International PCT Application PCT/US2014/050928 filed Aug. 13, 2014.
Sekiguchi, et al. "Molecular Weight Dependency of Antimicrobial Activity by Chitosan Oligomers"Food Hydrocolloids: Structures, Properties and Functions, 1994, pp. 71-76.
Choi, et al. "In Vitro Antimicrobial Activity of a Chitooligosaccharide Mixture Against Actinobacillus Actinomycetemcomitans and *Streptococcus Mutans*"International Journal of Antimicrobial Agents, vol. 18, 2001, pp. 553-557.

* cited by examiner

*Primary Examiner* — Walter E Webb
(74) *Attorney, Agent, or Firm* — Sorell, Lenna & Schmidt LLP; William D. Schmidt, Esq.

(57) ABSTRACT

An oral composition is provided comprising crosslinked polyvinylpyrrolidone (PVP) and xylitol. The xylitol and the crosslinked PVP are in a ratio of about 5:1, and the oral composition is in the form of a lozenge or lollipop. Methods are also provided.

23 Claims, 14 Drawing Sheets

METHODS AND COMPOSITIONS FOR PREVENTING AND TREATING TOOTH EROSION

This application claims priority to U.S. patent application Ser. No. 15/657,791, filed on Jul. 24, 2017, entitled "Methods and Compositions for Preventing and Treating Tooth Erosion," which is a continuation of U.S. patent application Ser. No. 14/771,222, now U.S. Pat. No. 9,744,108, filed on Aug. 28, 2015, entitled "Methods and Compositions for Preventing and Treating Tooth Erosion," which claims priority to PCT/US2014/019447, filed on Feb. 28, 2014, entitled "Methods and Compositions for Preventing and Treating Tooth Erosion," which claims priority to U.S. Provisional Application Ser. No. 61/770,863, filed Feb. 28, 2013, entitled "Methods and Compositions For Preventing and Treating Tooth Erosion." These applications are incorporated herein by reference into the present disclosure.

FIELD

The present invention relates to methods and compositions for preventing and treating tooth erosion.

BACKGROUND

Dental erosion is a significant oral health problem that affects millions of individuals around the world. Erosive tooth wear can cause significant tooth damage compromising the esthetics and function of teeth, requiring extensive dental treatment. Typically, dental erosion is caused by direct contact of intrinsic or extrinsic acid exposure to natural tooth enamel. Erosive tooth wear is a form of chemical tooth loss that causes enamel dissolution without involvement of bacterial origin. (Imfeld, 1996). Oral health problems associated with dental erosion of teeth have become more prevalent in recent years due to the popularity of diets high in acidic contents, increase in use of medication causing low salivary flow and systemic conditions such as gastro esophageal reflux disease (GERD) and Bulimia. Erosion no longer affects only the elderly population but can manifest in all age groups of our society. Acids either from intrinsic or extrinsic origin can soften tooth enamel Softening of the enamel surface is an early manifestation of acid erosion. Subsequently, the tooth structures are dissolved layer by layer or by a mechanical insult, resulting in bulk-loss of tooth material.

Erosive tooth wear from hydrochloric acid when stomach juice is involuntarily regurgitated has been associated with chronic health issues such as in GERD, hiatal hernia, or occur through chronic vomiting like in bulimia nervosa (Schroeder et al., 1995; Valena and Young, 2002; Barron et al., 2003). Prevalence of dental erosion in GERD patients is approximately 24% (Pace et al., 2008). According to the National Eating Disorders Association, approximately 30 million Americans suffer from eating disorders. (Eating Disorders and their Precursors, www.NationalEatingDisorders.org 2015. Moderate to advanced erosion and tooth wear present on the lingual and incisal edges of a patient's upper anterior teeth are manifestations of a systemic condition such as Bulimia and GERD. The majority of these patients require extensive restorative work to return the teeth to optimal function and esthetics.

Various products containing fluoride and/or calcium phosphate are readily available for caries prevention and acid erosion. However, these products are commonly toothpastes that claim to help re-mineralization and may lead to further damage to tooth erosion by abrasion, resulting from brushing immediately after an acidic regurgitation. Anti-erosive mouthwashes are also currently available that claim to help re-mineralization. However, a large majority of these mouthwashes contain alcohol and have a low pH or acidic content that can contribute to further demineralization of the tooth structure. Rinses and gels are also commonly used to address the re-mineralization of teeth by providing fluoride as a rinse or gel, but none of the products available address neutralizing the acidity of saliva, which is the natural medium of teeth. Preventive treatments that can reduce tooth damage from hydrochloric acid erosion will certainly benefit patients suffering from acid erosion of the teeth (e.g., patients suffering from GERD, eating disorders, drinking excessive amounts of acidic drinks, etc.)

Additionally, the shelf-life and practicality of these products for everyday use by consumers immediately after an acidic episode reduces the practicality of these products.

Accordingly, there is a need for compositions and methods to prevent and treat tooth erosion in patients exhibiting tooth damage. Patients suffering from conditions such as GERD or Bulimia are in need of compositions and methods for treating tooth erosion. Compositions and methods are also needed to re-harden and re-mineralize the teeth while also providing an extended shelf-life. There is also a need for these compositions to be administered in the form of lollipops and lozenges so that a patient can be treated with these compositions for a longer period of time than the currently available products. The compositions administered via lollipops and lozenges can stimulate salivary flow, neutralize the saliva and administer re-mineralization components so that a more effective remineralization can take place.

SUMMARY

New compositions and methods are provided that effectively prevent, treat and reduce tooth erosion in patients suffering from conditions that increase the acidity in the oral cavity, such as GERD and Bulimia.

In one embodiment, an oral composition is provided. The oral composition comprises crosslinked polyvinylpyrrolidone (PVP) and xylitol, and the xylitol and crosslinked PVP are in a ratio of about 5:1. The oral composition is in the form of a lozenge or lollipop.

In one embodiment, an oral composition for neutralizing saliva and re-hardening tooth enamel is provided. The oral composition comprises an alkalinizing agent, a re-mineralizing agent, a base, a plasticizer, and a sugar alcohol. The oral composition is in the form of a lozenge or a lollipop. The base comprises crosslinked polyvinylpyrrolidone (PVP), the plasticizer comprises glycerin, and the sugar alcohol comprises xylitol.

In an exemplary embodiment, a multi-layer lozenge or lollipop for neutralizing saliva and re-hardening tooth enamel is provided. The lozenge or lollipop comprises an alkalinizing agent, a re-mineralizing agent, a base, a plasticizer, and a sugar alcohol. The lozenge or lollipop upon oral administration raises the saliva pH from about 7 to about 10 in about 1 minute. The multi-layer lozenge or lollipop further comprises an inner core and an outer layer, and upon oral administration the lollipop is dissolved within about 20 minutes. The base comprises crosslinked polyvinylpyrrolidone (PVP), the plasticizer comprises glycerin, and the sugar alcohol comprises xylitol.

In another embodiment, a method of making a multi-layer lozenge or lollipop for neutralizing saliva and re-hardening tooth enamel is provided. The method comprises: molding an inner core, the inner core comprising, xylitol, crosslinked polyvinylpyrrolidone (PVP), and glycerin; and molding an outer layer over the inner core, the outer layer comprising xylitol, crosslinked PVP, glycerin, and L-arginine. Molding the inner core further comprises congealing the inner core in a mold for a period of time, and then inserting a stick into a portion of the inner core, and after the inserting of the stick into a portion of the inner core, the outer layer is then molded over the inner core.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1A:
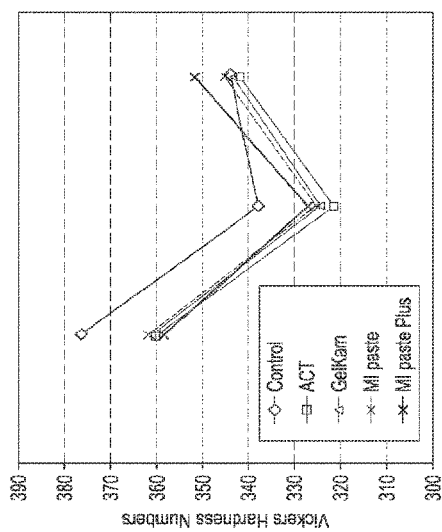
FIG. 1A and FIG. 1B illustrate the effect of various commercial products verses no treatment (control) on the hardness recovery of softened tooth enamel.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "an alkalinizing agent" includes one, two, three or more alkalinizing agents.

The term "lozenge," as used herein, describes a solid or semi-solid substance that is dissolvable in the mouth. A lozenge can include, but is not limited to, a tablet, a troche, a cachou, pill, capsule, tab, a pellet, a dragee and/or a pastille.

The term "lollipop," as used herein, describes a solid or semi-solid substance that is dissolvable in the mouth and is mounted on a stick.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

Alkalinizing Agent

Alkalinizing agents are useful for neutralizing acids of the oral cavity. Alkalinizing agents can buffer the acids in the mouth and raise pH levels in acidic saliva from as low as 1.0 to 6.8 or greater. For example, treatment can be started when saliva pH is about 1.0, 1.5, 2.0, 2.5, 3.0, 3.5, 4.0, 4.5 or 5.0. The process of using an alkalinizing agent is useful for preventing and treating tooth erosion. Examples of alkalinizing agents include, but are not limited to, arginine, sodium carbonate, sodium bicarbonate, potassium carbonate, potassium bicarbonate, calcium carbonate, calcium bicarbonate, sesquicarbonates, borates, silicates, phosphates (e.g., monosodium phosphate, trisodium phosphate, pyrophosphate salts, etc.), imidazole or combinations thereof.

Saliva is a naturally occurring alkalinizing agent. Salivation is enhanced by agents stimulating the salivary glands. Saliva is the most significant natural defense in the oral cavity and is well known to possess several tooth-protective properties including antibacterial action, buffering capacity, cleansing effect, and re-mineralization activity.

In some embodiments, the alkalinizing agents may also comprise licorice root, eucalyptus or arginine from about 1%, 2%, 3%, 4%, 5%, 6%, 7% or to about 8%.

Alkalinizing agents may also comprise a re-hardening agent and buffering agent. Re-hardening of tooth enamel occurs when an agent capable of hardening tooth enamel is applied to the teeth after an acidic challenge to the teeth, which softens the enamel Re-hardening agents are substances which are applied to the teeth to harden the softened enamel Examples of re-hardening agents include, but are not limited to, green tea extract, calcium phosphate, fluoride, sodium fluoride, stannous fluoride, calcium chloride, potassium phosphate, casein phosphopeptide, caseinates, digests thereof or casein-derived phosphopeptides, amorphous calcium phosphate or combinations thereof. Enamel re-hardening is indicative of the effectiveness of various preventive treatments.

In some embodiments, the alkalinizing agent discussed above can be in the composition from about 0.01%, 0.05%, 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% to about 10% % w/w, w/v, or v/v.

In some embodiments, the alkalinizing agent can raise the pH of saliva to above about 6.0, 6.5, 7.0, 7.5, 8.0, 8.5, 9.0, to about 9.5 or higher if desired.

In some embodiments, the rehardening agents can be in the composition from about 0.01%, 0.05%, 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% to about 10% % w/w, w/v, or v/v.

In some embodiments, buffering agents include sodium chloride, 4-(2-hydroxyethyl)-1-piperazineethanesulfonic acid (HEPES), potassium hydroxide, potassium chloride, carboxylic, phosphoric and sulfonic acids, acid salts (e.g., monosodium citrate, disodium citrate, monosodium malate, etc.) or combinations thereof. Buffering agents can be added to the composition at concentrations of about 1 mM to about 300 mM. Buffering agents are added in sufficient quantity to adjust the pH of the composition from about 1.0 to 6.8, 6.9, 7.0 or greater.

Remineralizing Agent

Re-mineralization is also useful for preventing and treating tooth erosion. Re-mineralization occurs when a mineral is added to the teeth to replace mineral components that have been depleted from the teeth. Softened enamel represents the stage of erosion where a remaining scaffold of mineral crystals can still be re-mineralized or re-hardened.[16]

Examples of re-mineralization agents include, fluoride, calcium, and/or phosphate. Fluoride enhances re-mineralization of early carious lesion by adsorbing onto the partially dissolved crystal lattice, which attracts calcium and phosphate ions to precipitate.[17] In vitro and in situ studies have shown that a single or repetitive exposure to fluoride month rinse, fluoride gel, or 5000 ppm fluoride toothpaste, could slow down or prevent the erosive process.[18-20] Fluoride, in the presence of calcium and phosphate, shifts the equilibrium surrounding the tooth surface towards re-mineralization.

In some embodiments, the re-mineralization agent comprises a stannous ion or a stannous ion source. Suitable stannous ion sources include without limitation stannous fluoride, other stannous halides such as stannous chloride dihydrate, stannous pyrophosphate, organic stannous carboxylate salts such as stannous foimate, acetate, gluconate, lactate, tartrate, oxalate, malonate and citrate, stannous ethylene glyoxide and the like. In some embodiments, one or more stannous ion sources are optionally present in the total amount of from about 0.01%, 0.05%, 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% to about 10% % w/w, w/v, or v/v.

In some embodiments, the re-mineralizing agents can be added to the composition at about 0.01%, 0.05%, 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% to about 10% % w/w, w/v, or v/v.

In some embodiments, the compositions of the present application further comprise an antimicrobial (e.g., antibacterial) agent. In some embodiments, one or more antimicrobial agents are optionally present. In some embodiments, one or more antimicrobial agents are optionally present in the amount of 0.05%, 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% to about 10% w/w, w/v/, v/v.

In some embodiments, one or more antimicrobial agents, including but not limited to, ester parabens such as methy paraben, ethyl paraben, propyl paraben, butyl paraben, benzyl paraben, or a combination thereof are optionally present in the amount of 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1%, 1.5%, 2%, 2.5% to about 3% w/w, w/v/, v/v. Some embodiments of the present invention optionally comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, sodium sulfite, disodium metabisulfite, sodium bisulfite, and mixtures thereof in an amount of about 0.1%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1%, 1.5%, 2%, 2.5% to about 3% w/w, w/v/, v/v.

In some embodiments, the compositions may comprise adhesion agents; viscosity modifiers; diluents; nonionic, cationic or amphoteric surfactants; foam modulators; humectants; mouth feel agents; sweeteners; flavoring agents; colorants, or combinations of two or more thereof.

The compositions of the present application are applied by the individual patient or the health care provider as an oral care composition, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity (e.g., increase pH, harden enamel, remineralize teeth, etc.). The oral care composition may be in various forms including toothpaste, dentifrice, tooth gel, subgingival gel, mouth rinse or mouth wash, mousse, foam, mouth spray, lozenge, lollipop, chewable tablet, chewing gum or denture product. In one embodiment, the oral care composition is in a form selected from toothpaste, dentifrice, tooth gel, mouth wash or denture product. The oral care composition may also be incorporated onto strips or films for direct application or attachment to oral surfaces.

In one embodiment, the oral care composition comprises a mouthwash that is applied in two stages. First a therapeutically effective amount of an alkalinizing agent is applied to the teeth so as to raise saliva pH to 7.0 or above; and then a therapeutically effective amount of a re-mineralizing agent is applied to the teeth.

A "therapeutically effective amount" or "effective amount" is such that when administered, the alkalinizing and re-mineralizing results in alteration of the effects of acid in the oral cavity, such as, for example, prevention of tooth erosion or reduction of tooth erosion, re-hardening and re-mineralization of tooth enamel, etc.

The terms "treating" and "treatment" include "preventing" or "prevention" of disease or undesirable condition. In addition, "treating" or "treatment" does not require complete alleviation of signs or symptoms, does not require a cure, and specifically includes protocols that have only a marginal effect on the patient. "Reducing erosion" includes a decrease in erosion and does not require complete alleviation of erosion signs or symptoms, and does not require a cure.

In various embodiments, reducing erosion includes 5%, 10%, 15%, 20%, 25%, 30%, 35%, 40%, 45% or higher decrease in erosion.

In some embodiments, the alkalinizing agent can be applied to the oral cavity for a time of from about 5, 10, 15, 20, 25, 30, 35, 40, 45, 50, 55 to about 60 seconds. The alkalinizing agent can be applied to the oral cavity at a volume of about 5, 10, 15, 20, 25, 30, 35, 40, 45, 50, 55, 60, 65, 70, 75, 80, 85, 90, 95 to a volume of about 100 milliliters (mL).

In some embodiments, the re-mineralizing agent can be applied to the oral cavity for a time of about 5, 10, 15, 20, 25, 30, 35, 40, 45, 50, 55 to about 60 seconds. The re-mineralizing agent can be applied to the oral cavity at a volume of about 5, 10, 15, 20, 25, 30, 35, 40, 45, 50, 55, 60, 65, 70, 75, 80, 85, 90, 95 to a volume of about 100 mL.

In some embodiments, the alkalinizing agent is an alkalinizing mouthwash. The pH of the alkalinizing mouthwash may be 8.0 or greater.

In some embodiments, a kit is provided that may include additional parts along with the dental compositions. The kit may include a first mouthwash (e.g., alkalinizing agent) in a first compartment. The second compartment may include a second mouthwash (re-mineralizing agent) to be used in the oral cavity and other devices for administering it (e.g., calibrated cups, stirrers, etc.). A third compartment may include other procedural supplies, as well as an instruction booklets or links to websites for product information. A cover of the kit may include illustrations of using the dental composition and a clear plastic cover may be placed over the compartments to maintain sterility.

Figure 5:
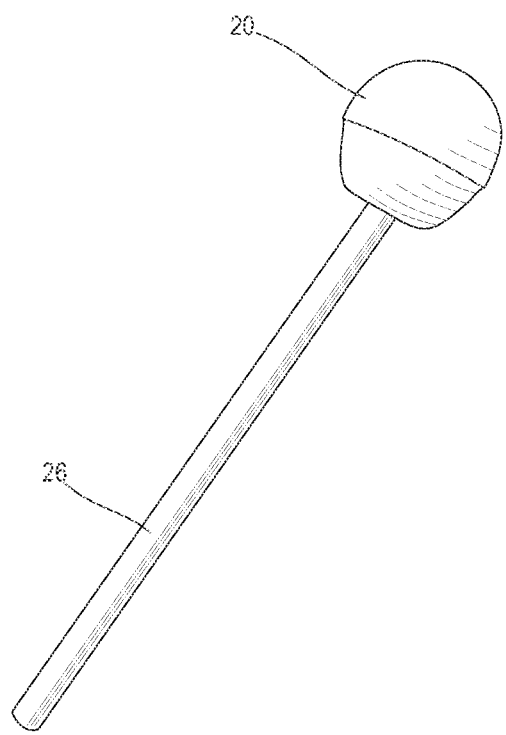
FIG. 5 is a top view of several multi-layer lollipops for neutralizing saliva and re-hardening tooth enamel.
Figure 6:
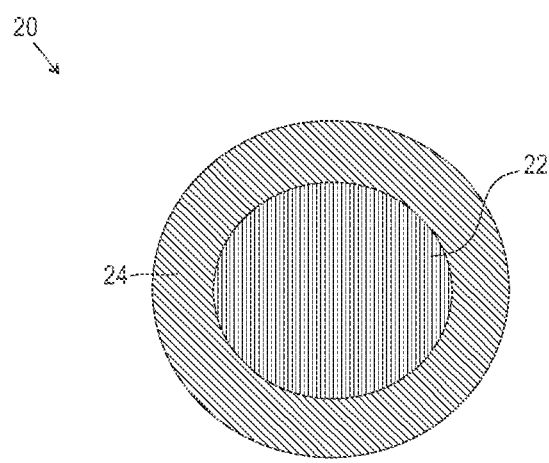
FIG. 6 is a cross-sectional view a multi-layer lollipop of FIG. 5.

In one embodiment, an oral composition for neutralizing saliva and re-hardening tooth enamel is provided. The composition comprises an alkalinizing agent, a re-mineralizing agent, a base, a plasticizer, and a sugar alcohol. The composition is in the form of a lollipop 20 or a lozenge, as shown in FIGS. 5 and 6.

The base comprises polyvinylpyrrolidone (PVP) such as Kollidon® or crosslinked PVP such as Kollidon® Cl, the plasticizer comprises glycerin, and the sugar alcohol comprises xylitol. The base enhances stability and release of the components of the composition. The combination of Kollidon® and xylitol allows for a lollipop or lozenge that has a stable melting point since the low melting point of xylitol (e.g., about 92° C.) is not further lowered by the use of Kollidon® (e.g., melting point of about >140° C.).

The base, such as, for example, PVP or the crosslinked PVP, is in an amount of from about 5 to about 50% of the composition. The base such as, for example, the PVP or the crosslinked PVP, may be in an amount of about 5 to about 40%, 5 to about 30%, 5 to about 20%, 5 to about 10%, 10 to about 50%, 10 to about 40%, 10 to about 30%, 10 to about 20%, 20 to about 50%, 20 to about 40%, 20 to about 30%, 30 to about 50%, 30 to about 40%, or 40 to about 50% of the composition. In some embodiments, the base such as, for example, the PVP or the crosslinked PVP, is in an amount of from about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% of the composition. In some embodiments, the base, such as, for example, the PVP or the crosslinked PVP, is in an amount of from about 1 to about 90% of the composition. In some embodiments, the base, such as, for example, the PVP or the crosslinked PVP is in an amount of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, to about 90% of the composition.

The sugar alcohol, such as, for example, the xylitol, is in an amount of from about 20 to about 95% of the composition. In some embodiments, the sugar alcohol, such as for example, the xylitol, is in an amount of about 20 to about 85%, 20 to about 75%, 20 to about 65%, 20 to about 55%, 20 to about 45%, 20 to about 35%, 30 to about 95%, 30 to about 85%, 30 to about 75%, 30 to about 65%, 30 to about 55%, 30 to about 45%, 40 to about 95%, 40 to about 85%, 40 to about 75%, 40 to about 65%, 40 to about 55%, 50 to about 95%, 50 to about 85%, 50 to about 75%, 50 to about 65%, 60 to about 95%, 60 to about 85%, 60 to about 75%, 70 to about 95%, 70 to about 85%, or 80 to about 95% of the composition. In some embodiments, the sugar alcohol, such as, for example, the xylitol, is in an amount of from about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95% of the composition.

The plasticizer, such as, for example, the glycerin, is in an amount of from about 0.1 to about 1% of the composition. In some embodiments, the plasticizer, such as, for example, the glycerin, is in an amount of about 0.1 to about 0.8%, 0.1 to about 0.6%, 0.1 to about 0.4%, 0.1 to about 0.2%, 0.3 to about 1%, 0.3 to about 0.8%, 0.3 to about 0.6%, 0.3 to about 0.4%, 0.5 to about 1%, 0.5 to about 0.8%, 0.5 to about 0.6%, 0.7 to about 1%, or 0.7 to about 0.8% of the composition. In some embodiments, the plasticizer, such as, for example, the glycerin is in an amount of from about 0.1, 0.2, 0.3, 0.4, 0.5, 0.6, 0.7, 0.8, 0.9, to about 1% of the composition. In some embodiments, the plasticizer, such as, for example, the glycerin, is in an amount of from about 0.1 to about 5% of the composition. In some embodiments, the plasticizer, such as, for example, the glycerin is in an amount of from about 0.1, 0.2, 0.3, 0.4, 0.5, 0.6, 0.7, 0.8, 0.9, 1, 2, 3, 4, to about 5% of the composition.

In some embodiments, the base and the sugar alcohol are in a particular ratio in the composition. For example, the xylitol and crosslinked PVP are in a 5:1 ratio. The crosslinked PVP can be Kollidon® Cl, and the xylitol and crosslinked PVP are in a 5:1 ratio. In some embodiments, the ratio of xylitol and crosslinked PVP can be from 10:1, 9:1, 8:1, 7:1, 6:1, 5:1, 4:1, 3:1 to about 2:1. In some embodiments, the oral composition can comprise only a sugar alcohol and a base in a 5:1 ratio.

In some embodiments, the base, can alternatively or in addition to the crosslinked PVP be hydroxypropyl methylcellulose (HPMC), methylcellulose, hydrophilic polymers for controlled release, and/or hydrophobic polymers. In some embodiments, the hydrophilic polymers, include, but are not limited to a polyacrylate, an alginate, chitosan, a hydrophilic polyamine, a chitosan derivative, polylysine, polyethylene, xanthan, carrageenan, chondroitin sulfate, a starch, a modified cellulosic polymer, a dextran, and/or hyaluronan. In some embodiments, the hydrophobic polymers include, but are not limited to, phthalic acid esters, polyvinyl acetate phthalate, cellulose acetate phthalate, methacrylic acid esters, cellulose ethers, polyethylene oxide polymers, and/or ethylcellulose.

In some embodiments, the plasticizer, can alternatively or in addition to the glycerin be polyethylene glycol (PEG), PEG 200, PEG 300, PEG 400, propylene glycol and/or citrate esters.

In some embodiments, the sugar alcohol can alternatively or in addition to the xylitol be sorbitol and/or mannitol.

The alkalinizing agent can include the alkalinizing agents described above and in the amounts disclosed. For example, the alkalinizing agent can comprise a re-hardening agent, eucalyptus oil, licorice root, and/or arginine, such as L-arginine.

The eucalyptus oil can be in an amount of from about 0.01 to about 0.5% of the composition. In some embodiments, the eucalyptus oil is in an amount of from about 0.01, 0.02, 0.03, 0.04, to about 0.5% of the composition. In some embodiments, the eucalyptus oil can be in an amount of from about 0.01 to about 3% of the composition. In some embodiments, the eucalyptus oil is in an amount of from about 0.01, 0.02, 0.03, 0.04, 0.5, 0.6, 0.7, 0.8, 0.9, 1, 2, to about 3% of the composition.

The licorice root can be in an amount of from about 0.01 to about 1% of the composition. In some embodiments, the licorice root can be in an amount of from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, to about 1% of the composition. In some embodiments, the licorice root can be in an amount of from about 0.01 to about 3% of the composition. In some embodiments, the licorice root can be in an amount of from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, to about 3% of the composition.

The arginine, such as L-arginine, can be in an amount of from about 1 to about 8% of the composition. In some embodiments, the arginine, such as L-arginine can be in an amount of from about 1, 2, 3, 4, 5, 6, 7, to about 8% of the composition. The arginine, such as L-arginine, can be in an amount of from about 1 to about 20% of the composition. In some embodiments, the arginine, such as L-arginine, can be in an amount of from about 1, 2, 3, 4, 5, 6, 7, 8, 9, 10, 11, 12, 13, 14, 15, 16, 17, 18, 19, to about 20% of the composition.

The alkalinizing agent can also include sodium bicarbonate, or potassium bicarbonate, and the re-hardening agent can include calcium chloride, potassium phosphate and/or casein phosphopeptide.

The alkalinizing agent, such as, for example, the casein phosphopeptide, can be in an amount of from about 1 to about 5% of the composition. In some embodiments, the alkalinizing agent, such as, for example, the casein phosphopeptide, can be in an amount of from about 1, 2, 3, 4, to about 5% of the composition. In some embodiments, the alkalinizing agent, such as, for example, the casein phosphopeptide, can be in an amount of from about 1 to about 20% of the composition. In some embodiments, the alkalinizing agent, such as, for example, the casein phosphopeptide, can be in an amount of from about 1, 2, 3, 4, 5, 6, 7, 8, 9, 10, 11, 12, 13, 14, 15, 16, 17, 18, 19, to about 20% of the composition.

The re-mineralizing agent can include the re-mineralizing agents described above and the amounts disclosed. For example, the re-mineralizing agent can include calcium chloride, monopotassium phosphate, and/or sodium fluoride.

The re-mineralizing agent, such as, for example, the calcium chloride, can be in an amount of from about 0.01 to about 0.5% of the composition. In some embodiments, the re-mineralizing agent, such as, for example, the calcium chloride, can be in an amount of from about 0.01 to about 0.2%, from about 0.01 to about 0.08%, from about 0.01 to about 0.04%, from about 0.03 to about 0.5%, from about 0.03 to about 0.5%, from about 0.03 to about 0.2%, from about 0.03 to about 0.08%, from about 0.03 to about 0.04%, from about 0.05 to about 0.5%, from about 0.05 to about 0.2%, from about 0.05 to about 0.08%, from about 0.07 to about 0.5%, from about 0.07 to about 0.2%, or from about 0.07 to about 0.8%. In some embodiments, the re-mineralizing agent, such as, for example, the calcium chloride, can be in an amount of from about 0.01, 0.02, 0.03, 0.04, 0.05, 0.06, 0.07, 0.08, 0.09, 0.1, 0.2, 0.3, 0.4 or 0.5% of the composition. In some embodiments, the re-mineralizing agent, such as, for example, the calcium chloride, can be in an amount of from about 0.01 to about 15% of the composition. In some embodiments, the re-mineralizing agent, such as, for example, the calcium chloride, can be in an amount of from about 0.01, 0.02, 0.03, 0.04, 0.05, 0.06, 0.07, 0.08, 0.09, 0.1, 0.2, 0.3, 0.4 or 0.5, 0.6, 0.7, 0.8, 0.9, 1, 2, 3, 4, 5, 6, 7, 8, 9, 10, 11, 12, 13, 14, to about 15% of the composition.

The re-mineralizing agent, such as, for example, the monopotassium phosphate can be in an amount of from about 0.01 to about 0.5% of the composition. In some embodiments, the re-mineralizing agent, such as, for example, the monopotassium phosphate, can be in an amount of from about 0.01 to about 0.2%, from about 0.01 to about 0.08%, from about 0.01 to about 0.04%, from about 0.03 to about 0.5%, from about 0.03 to about 0.5%, from about 0.03 to about 0.2%, from about 0.03 to about 0.08%, from about 0.03 to about 0.04%, from about 0.05 to about 0.5%, from about 0.05 to about 0.2%, from about 0.05 to about 0.08%, from about 0.07 to about 0.5%, from about 0.07 to about 0.2%, or from about 0.07 to about 0.8%. In some embodiments, the re-mineralizing agent, such as, for example, the monopotassium phosphate, can be in an amount of from about 0.01, 0.02, 0.03, 0.04, 0.05, 0.06, 0.07, 0.08, 0.09, 0.1, 0.2, 0.3, 0.4 or 0.5% of the composition. In some embodiments, the re-mineralizing agent, such as, for example, the monopotassium phosphate, can be in an amount of from about 0.01 to about 15% of the composition. In some embodiments, the re-mineralizing agent, such as, for example, the monopotassium phosphate, can be in an amount of from about 0.01, 0.02, 0.03, 0.04, 0.05, 0.06, 0.07, 0.08, 0.09, 0.1, 0.2, 0.3, 0.4 or 0.5, 0.6, 0.7, 0.8, 0.9, 1, 2, 3, 4, 5, 6, 7, 8, 9, 10, 11, 12, 13, 14, to about 15% of the composition.

The re-mineralizing agent, such as, for example, the sodium fluoride, can be in an amount of from about 0.01 to about 1% or from about 0.01 to about 0.1% of the composition. In some embodiments, the re-mineralizing agent, such as, for example, the sodium fluoride, can be in an amount of from about 0.01 to about 0.5%, from about 0.01 to about 0.08%, from about 0.01 to about 0.04%, from about 0.03 to about 0.1%, from about 0.03 to about 0.5%, from about 0.03 to about 0.2%, from about 0.03 to about 0.08%, from about 0.03 to about 0.04%, from about 0.05 to about 1%, from about 0.05 to about 0.5%, from about 0.05 to about 0.2%, from about 0.05 to about 0.08%, from about 0.07 to about 1%, from about 0.07% to about 0.5%, from about 0.07 to about 0.2%, or from about 0.07 to about 0.8%. In some embodiments, the re-mineralizing agent, such as, for example, the sodium fluoride, can be in an amount of from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1% of the composition. In some embodiments, the re-mineralizing agent, such as, for example, the sodium fluoride, can be in an amount of from about 0.01 to about 15% of the composition. In some embodiments, the re-mineralizing agent, such as, for example, the sodium fluoride, can be in an amount of from about 0.01, 0.02, 0.03, 0.04, 0.05, 0.06, 0.07, 0.08, 0.09, 0.1, 0.2, 0.3, 0.4 or 0.5, 0.6, 0.7, 0.8, 0.9, 1, 2, 3, 4, 5, 6, 7, 8, 9, 10, 11, 12, 13, 14, to about 15% of the composition.

The composition is administered to a user's teeth in the form of a lollipop or lozenge for a time of from about 1 to about 20 minutes. The composition is administered to a user's teeth for a period of time of from about 1, 2, 3, 4, 5, 6, 7, 8, 9, 10, 11, 12, 13, 14, 15, 16, 17, 18, 19, to about 20 minutes.

The composition raises the user's saliva pH to about 7 or greater in about 1 minute. In some embodiments, the composition raises the user's saliva pH to about 7, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.

The composition can also include green tea extract in an amount of from about 0.01 to about 1%. In some embodiments, the green tea extract is in an amount of from about 0.01, 0.02, 0.03, 0.04, 0.05, 0.06, 0.07, 0.08, 0.09, to about 1% of the composition. In some embodiments, the composition can also include green tea extract in an amount of from about 0.01 to about 5%. In some embodiments, the green tea extract is in an amount of from about 0.01, 0.02, 0.03, 0.04, 0.05, 0.06, 0.07, 0.08, 0.09, 1, 2, 3, 4, to about 5% of the composition.

As described above, the composition is in the form of a lollipop of lozenge. In some embodiments, a multi-layer lollipop 20 is provided that is formed from the composition. The lollipop comprises an inner core 22, an outer layer 24 and a stick 26. The lollipop is configured to be inserted into a patient's mouth to stimulate salivary flow of a patient, neutralize the patient's saliva, and as the patient sucks and continues to suck on the lollipop, the lollipop releases components of the composition to assist in replenishing softened enamel in the teeth. The lollipop is able to stay in the mouth of a patient for a longer period of time than toothpastes and/or mouthwashes, thereby increasing the effectiveness of teeth re-mineralization. In some embodiments, upon oral administration, the lollipop dissolves in about 20 minutes.

The lollipop can be formed from the composition via molding methods described herein. Since the lollipop is formed from the composition, the amount of each component in the lollipop will be the same as in the composition, as described above. In some embodiments, the inner core of the lollipop is formed before the outer layer, and comprises components of the composition, such as, a sugar alcohol, a base, one or more alkalinizing agents, one or more re-mineralizing agents, a plasticizer, and an extract such as green tea extract.

In one embodiment, the inner core of the lollipop comprises xylitol, crosslinked PVP, such as Kollidon® Cl, sodium fluoride, monopotassium phosphate, calcium chloride, glycerin, green tea extract, licorice extract, eucalyptus oil, and casein phosphopeptide.

In some embodiments, the outer layer of the lollipop is formed after the inner core, and is then molded over the inner core. The outer layer comprises components of the composition, such as, a sugar alcohol, a base, a plasticizer, one or more alkalinizing agents, and an extract such as green tea extract.

In one embodiment, the outer layer comprises xylitol, crosslinked PVP, such as Kollidon® Cl, glycerin, green tea extract, licorice extract, eucalyptus oil and L-arginine.

In some embodiments, a multi-layered lollipop or lozenge is provided that comprises crosslinked PVP and xylitol, or crosslinked PVP, xylitol and glycerin where the ratio of xylitol to crosslinked PVP is 5:1. In this embodiment, any of the components described above may be added to the lollipop or lozenge, as well as any other active pharmaceutical ingredients contemplated.

In some embodiments, the multi-layered lollipop can have more than 2 layers. In some embodiments, the multi-layered lollipop can have 2, 3, 4, 5, 6, 7, 8, 9, or 10 layers depending on the release desired. In one embodiment, the lollipop can be a single monolithic lollipop with no layers.

The lollipop as described above, is administered to a user's teeth for a period of time of from about 1 to about 20 minutes. The lollipop is administered to a user's teeth for a time of from about 1, 2, 3, 4, 5, 6, 7, 8, 9, 10, 11, 12, 13, 14, 15, 16, 17, 18, 19, to about 20 minutes. The re-mineralizing agents, such as, for example, the calcium chloride and the monopotassium phosphate contained in the lollipop will release during the period time of from about 1 to about 20 minutes to assist in the replenishing of softened tooth enamel, and the sodium fluoride will assist in remineralization of tooth structures.

In some embodiments, the outer layer, the inner layer and/or the stick of the lollipop can be naturally dyed to have various colors such as pink, peach, red, white, yellow, orange, purple, green and/or blue. In some embodiments, the outer layer and the inner layer can be naturally dyed in the same or different colors. In some embodiments, the dyes are made so as not to stain the patient's teeth.

In some embodiments, the components of the lollipop can be released from the lollipop via controlled and/or immediate release over the period of time of from about 1 to about 20 minutes, described herein. In some embodiments, the components of the lollipop may be released via microspheres.

In some embodiments, a lollipop or lozenge is provided that is single layered. The single layered lozenge or lollipop comprises a neutralizing basic salt, such as, for example, arginine on an outer layer that initially dissolves with a patient's saliva, neutralizing the acidity caused by consumption of a low pH food or acidic regurgitation. The single layered lollipop or lozenge also includes a base comprising PEG 1440, calcium chloride, monopotassium phosphate, sodium fluoride, casein, green tea extract, xylitol, and licorice extract.

In some embodiments, a lollipop or lozenge is provided that is multi-layered. In some embodiments, the liquid mouthwash described herein is made into a solid lollipop or lozenge. In some embodiments, a mold is used to form the lollipop or lozenge, and the lollipop or lozenge can weigh up to 10 g. The multi-layered lollipop or lozenge comprises a neutralizing basic salt in the outer layer, such as, for example, arginine, and licorice extract; a second neutralizing layer comprising a protein, such as, for example, casein, green tea extract, xylitol, and a base comprising PEG 1440; and a soft gelatin core of calcium chloride, monopotassium phosphate, sodium fluoride and PEG 1440. The neutralizing basic salt on the outer layer initially dissolves with the saliva, neutralizing the acidity caused by consumption of a low pH food or acidic regurgitation. The protein (e.g., casein) in the second layer continues with neutralization and also provides calcium. The softer consistency of the gelatin core comprising the calcium chloride, monopotassium phosphate, sodium fluoride replenishes the mineral deficit in the teeth and also helps with the remineralization process. Table 1 below illustrates the components and the particular amounts used in the single layered and multi-layered lollipops and lozenges.

TABLE 1

Components of the single layer and Multi-layer Lollipop and Lozenge

| | | Per 240 ml solution | Per 10 ml solution |
|---|---|---|---|
| Active Ingredient | arginine | 4.80 g | 0.2 g |
| | casein | 4.80 g | 0.2 g |
| | calcium chloride (CaCl$_2$) | 0.0530 g | 0.0022 g |
| | monopotassium phosphate (KH$_2$PO$_4$) | 0.0292 g | 0.0012 g |
| | sodium fluoride (NaF) | 6 ml of 10,000 ppm = 0.06 g | 0.0025 g |
| | Green tea extract | 8 drops | 0.5 drop |
| Additional Ingredients (for taste) | Xylitol | 2.5 g | 0.104 g |
| | Licorice extract | 8 drops | 0.5 drop |
| | Eucalyptus Oil | 8 drops | 0.5 drop |

Method of Making

In some embodiments, a method of making a multi-layer lollipop for neutralizing saliva and re-hardening tooth enamel is provided. The method comprises: molding an inner core, the inner core comprising, xylitol, crosslinked polyvinylpyrrolidone (PVP), and glycerin; and molding an outer layer over the inner core, the outer layer comprising xylitol, crosslinked PVP, glycerin, and L-arginine. In some embodiments, the inner core further comprises sodium fluoride, monopotassium phosphate, calcium chloride, green tea extract, licorice extract, eucalyptus oil, and casein phosphopeptide; and the outer layer further comprises green tea extract, licorice extract, and eucalyptus oil.

In some embodiments, molding the inner core further comprises congealing the inner core in a mold for a period of time, and then inserting a stick into a portion of the inner core, and after the inserting of the stick into a portion of the inner core, the outer layer is then molded over the inner core.

In some embodiments, a method of making a multi-layer lollipop for neutralizing saliva and re-hardening tooth enamel is provided. The method comprises: molding an inner core, the molding of the inner core comprising, adding an amount of xylitol to a glass container, heating the xylitol to a temperature of 150° C. until the xylitol becomes clear, stirring the xylitol until it is mostly melted, adding an amount of crosslinked PVP to the glass container to form a mixture, stirring the mixture until it becomes thick, evenly adding an amount of sodium fluoride to the mixture, evenly adding an amount of monopotassium phosphate to the mixture, quickly and evenly adding an amount of calcium chloride to the mixture, adding an amount of glycerin to the mixture, sequentially adding an amount of green tea extract, an amount of licorice extract and then an amount eucalyptus oil to the mixture, quickly adding and mixing casein phosphopeptide to the mixture, pouring the mixture into a mold immediately after the casein phosphopeptide is mixed into the mixture, congealing the mixture at room temperature for a period time of from about 24 to about 48 hours, and inserting lollipop sticks into the congealed mixture after a period of time; and molding the outer layer onto the inner core, the molding of the outer layer comprising, adding an amount of xylitol to a glass container, heating the xylitol to a temperature of 150° C. until the xylitol becomes clear, stirring the xylitol until it is mostly melted, adding an amount of crosslinked PVP to the glass container to form a mixture, adding an amount of glycerin to the mixture, sequentially adding an amount of green tea extract, an amount of licorice extract and then an amount eucalyptus oil to the mixture, quickly adding and mixing L-arginine to the mixture, pouring the mixture into the mold immediately after the L-arginine is mixed into the mixture, and congealing the mixture at room temperature for a period time of from about 24 to about 48 hours to form the multi-layered lollipop.

Conditions Associated with Dental Erosion

Patients with certain chronic health conditions have been shown to have significantly higher erosive tooth wear than a control group.[11] Erosive tooth wear from hydrochloric acid when stomach juice is involuntarily regurgitated has been associated with chronic health issues such as in GERD, hiatal hernia, or occur through chronic vomiting like in bulimia nervosa (Schroeder et al., 1995; Valena and Young, 2002; Barron et al., 2003). Prevalence of dental erosion in GERD patients was 24% (Pace et al., 2008). Preventive treatments that can reduce tooth damage from hydrochloric acid erosion will certainly benefit patients suffering from stomach acid regurgitation due to GERD and eating disorders. According to the National Eating Disorders Association, approximately 30 million Americans suffer from eating disorders. The acts of alkalinizing, re-hardening and re-mineralizing are important in treating and preventing dental erosion in patients suffering from these diseases and in need of such treatment. An acidic challenge in a patient suffering from GERD or bulimia, can cause an under saturation of salivary salts (calcium, phosphate), which can contribute to the demineralization of tooth structure.[9,10] Delivery of these minerals to the oral environment by self-application through a mouth rinse or tooth cream is a practical approach for patients with acid regurgitation.

EXAMPLES

Studies were conducted to examine the ability of various treatments to increase the hardening of tooth enamel initially softened by hydrochloric acid (HCl). Further studies were conducted to study the hardness recovery of enamel softened by HCl and remineralized in saliva or artificial saliva after rinsing with sodium bicarbonate and fluoride.

Example 1: Investigation of Treatments to Improve Hardness Recovery of Softened Enamel This in-vitro study investigated the ability of four treatments to increase the hardening of tooth enamel initially softened by hydrochloric (HCl) acid. The treatments utilized products that contain calcium, phosphate, and/or fluoride, and were compared with hardening by saliva alone.

Methods

Extracted human molars were embedded in acrylic resin and polished. Vickers surface hardness (VH) was measured at each stage in the experiment. After $VH_{baseline}$, the teeth were bathed in a 10 mM HCl solution for 10 minutes to mimic regurgitated stomach acid, and $VH_{softening}$ was recorded. The acid-challenged teeth underwent treatment with the following products: 0.05% sodium fluoride mouth rinse (ACT; Chattem, Inc., Chattanooga, Tenn.), 0.4% stannous fluoride gel (Gel-Kam; Colgate-Palmolive, New York, N.Y.), casein phosphopeptide amorphous calcium phosphate (CPP-ACP) (MI-paste; GC America, Alsip, Ill.), fluoridated CPP-ACP paste (MIPlus; GC America, Alsip, Ill.). Deionized water was used as a control. Following treatment, teeth were bathed in human saliva for 1 hour, and $VH_{hardening}$ was recorded. Statistical analysis was performed with ANOVA followed by Student-Newman-Keuls post-hoc tests (p=0.05). VH (mean±standard deviation) are presented in Table 2.

Results

TABLE 2

Vickers Hardness in extracted human molars

|  | $VH_{baseline}$ | $VH_{softening}$ | $VH_{hardening}$ |
|---|---|---|---|
| Control | 376 ± 18 $^a$ | 338 ± 20 $^b$ | 344 ± 29 $^b$ |
| ACT | 360 ± 32 $^a$ | 321 ± 32 $^b$ | 342 ± 33 $^{a,\,b}$ |
| Gel-Kam | 361 ± 18 $^a$ | 325 ± 32 $^b$ | 343 ± 25 $^{a,\,b}$ |
| MI-paste | 362 ± 15 $^a$ | 325 ± 7 $^b$ | 345 ± 20 $^c$ |
| MI-Plus | 358 ± 19 $^a$ | 327 ± 14 $^b$ | 352 ± 29 $^a$ |

Figure 1B:
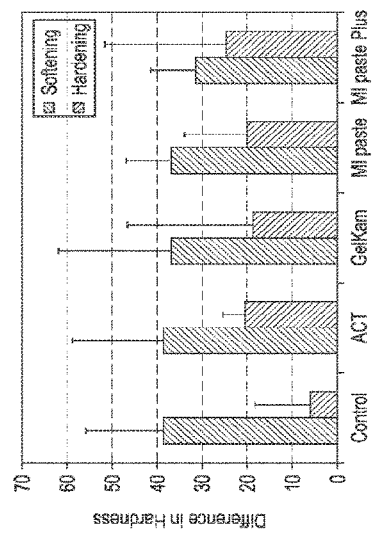

*Same superscript letter denotes hardness values that were not significantly different among experimental stages within the same group Now referring to Table 2 and FIGS. 1A and 1B, VH significantly decreased after HCl-challenge in all groups. After re-mineralization, VH increased significantly in MI-paste and MI-Plus groups, but not in the Control, ACT, and Gel-Kam. Only MI-Plus recovered the baseline VH-value.

Conclusion

Hardness recovery of enamel softened by HCl was minimal with saliva alone. The treatment that incorporated fluoride and calcium phosphate was the most effective for enamel hardness recovery.

Example 2: Hardness Recovery after Treatment with Sodium Bicarbonate and Fluoride In this example, we study the hardness recovery of enamel softened by hydrochloric acid and remineralized in saliva or artificial saliva after rinsing with sodium carbonate and fluoride.

Methods

The effect of acid reflux on enamel was mimicked by immersing extracted human molar in 10 mM hydrochloric acid pH 2.5 for 10 minutes followed by rinsing with tap water or a sodium bicarbonate solution. The re-mineralization phase was carried out by 1 min application of sodium fluoride rinse (ACT) followed by one-hour immersion in artificial saliva containing calcium and phosphate or pooled human saliva (IRB #10-01122-XM). Enamel surface hardness (Vickers) was measured at baseline, softening, and re-mineralization stages. Percent hardness recovery was calculated and subjected to ANOVA followed by Student-Newman-Keuls post-hoc test (p=0.05). N=10. Vickers hardness and percent hardness recovery (mean±standard deviation) are shown in Table 3.

Results

TABLE 3

Vickers Hardness and Hardness Recovery

|  | water rinse + F-rinse/ artificial saliva | Sodium bicarbonate solution + F-rinse/ artificial saliva | water rinse + F-rinse/ saliva | Sodium bicarbonate solution + F-rinse/saliva |
|---|---|---|---|---|
| Baseline hardness | 392 ± 11 $^A$ | 388 ± 15 $^A$ | 392 ± 13 $^A$ | 382 ± 14 $^A$ |
| HCl/rinse hardness | 327 ± 21 $^B$ | 335 ± 18 $^B$ | 315 ± 22 $^B$ | 311 ± 21 $^B$ |
| Remin hardness | 357 ± 11 $^C$ | 369 ± 13 $^C$ | 348 ± 11 $^C$ | 356 ± 13 $^C$ |
| % hardness recovery | 44.9 ± 17.5 $^a$ | 67.9 ± 15.4 $^b$ | 40.5 ± 14.9 $^a$ | 63.6 ± 18.6 $^b$ |

Hardness significantly decreased after HCl immersion and significantly increased after re-mineralization in all groups (uppercase superscript letters). Sodium bicarbonate solution plus fluoride rinse significantly increased percent hardness recovery in comparison to water plus fluoride rinse in both artificial saliva and human saliva (lowercase superscript letters).

TABLE 4

Formula for Artificial Saliva

To make 100 mL artificial saliva, combine the following:

100 ml deionized water
0.0221 g 1.5 mM $CaCl_2 \cdot 2H_2O$
0.0122 g 0.9 mM $KH_2PO_4$
0.4766 g 20 mM HEPES buffer
0.9693 g 130 mM KCl
few drops 1M KOH to adjust to pH 7.0
Formula modified from: Mukai Y, Lagerweij MD, ten Cate JM. Effect of a solution with high fluoride concentration on re-mineralization of shallow and deep root surface caries in vitro. Caries Res 2001; 35: 317-324.

Conclusion

The sodium bicarbonate solution and fluoride rinse improved the hardness recovery of enamel softened by hydrochloric acid.

Example 3: Buffering Capacity of Saliva in the Presence of HCl, and the Effectiveness of Sodium Bicarbonate in Neutralizing Acidic Saliva Dental erosion is caused by direct contact of intrinsic or extrinsic acid exposure to natural tooth enamel Highly acidic gastric juices (pH 1.0-3.0) are present in the saliva of patients suffering from Anorexia or Bulimia. The pH of the mouth may drop from a neutral pH of 6.8 or 7.0 to as low as 2.5 to 3.0. Patients suffering from Bulimia may rummage several times a day causing damage of their natural tooth structure. In presence of acidic substances in the mouth, the salivary glands increase production of saliva that is the body's natural buffering defense system to neutralize the acid. In a healthy individual with normal salivary flow it may take several hours to neutralize the oral cavity, during these few hours the teeth are exposed to an acidic medium, which accelerates the erosion process. Unfortunately patients suffering from eating disorders, acid reflux, and morning sickness due to pregnancy are usually clinically dehydrated and as a result may have lower than normal salivary flow. This may result in even longer period of time required by saliva to normalize the acidity of the mouth.

The majority of the preventive dental products in the market contain fluoride that provides help in re-mineralization of teeth exposed to an acidic medium. However, none of the commercially available products address the acidity of the Saliva resulting from vomiting with Bulimia, or acid regurgitation in patients with Reflux.

The formulated mouth wash described helps neutralize the saliva first and further helps in re-mineralization by replacing the mineral components depleted after an acidic challenge. The formulated mouth wash contains sodium bicarbonate, Eucalyptus oil, arginine and several other components including artificial saliva. The treatment includes a two-step system.

First Step:

Neutralize the oral cavity and saliva.

Second Step:

Rinse with fluoride, calcium and phosphate mixture to re-mineralize and harden the enamel.

Methods

Figure 2:
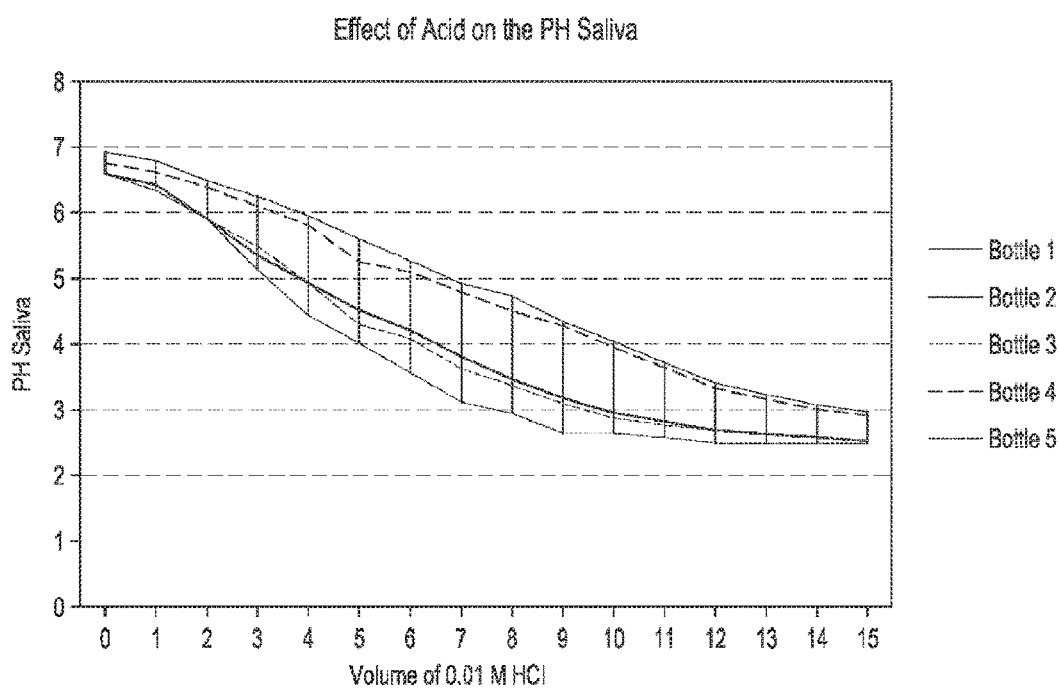
FIG. 2 illustrates the buffering capacity of saliva in the presence of hydrochloric acid.

The capacity of sodium bicarbonate to neutralize acid saliva was assessed. A pool of saliva was collected from 5 individuals, and the normal pH of the saliva was measured before brushing or eating. The average pH of the saliva was 6.8. In order to simulate an acidic challenge, the pH of the saliva was adjusted to 2.5 with 0.01M HCl. FIG. 2 graphically illustrates the effect of the acid on the pH of saliva.

A common recommendation made by dentists to patients suffering from Bulimia is to rinse their mouth with water after an acidic challenge, hoping water will wash away or dilute the acid and the buffering capacity of saliva will neutralize the remaining acid.

The results of this experiment shows that water alone is not effective in increasing the pH of the saliva to the neutral pH of 6.5-7, and the natural buffering effect of saliva is not enough to raise the pH.

The saliva was titrated with a 3M sodium bicarbonate solution and measured the volume of solution necessary to neutralize the saliva to a pH of 6.8.

Figure 3:
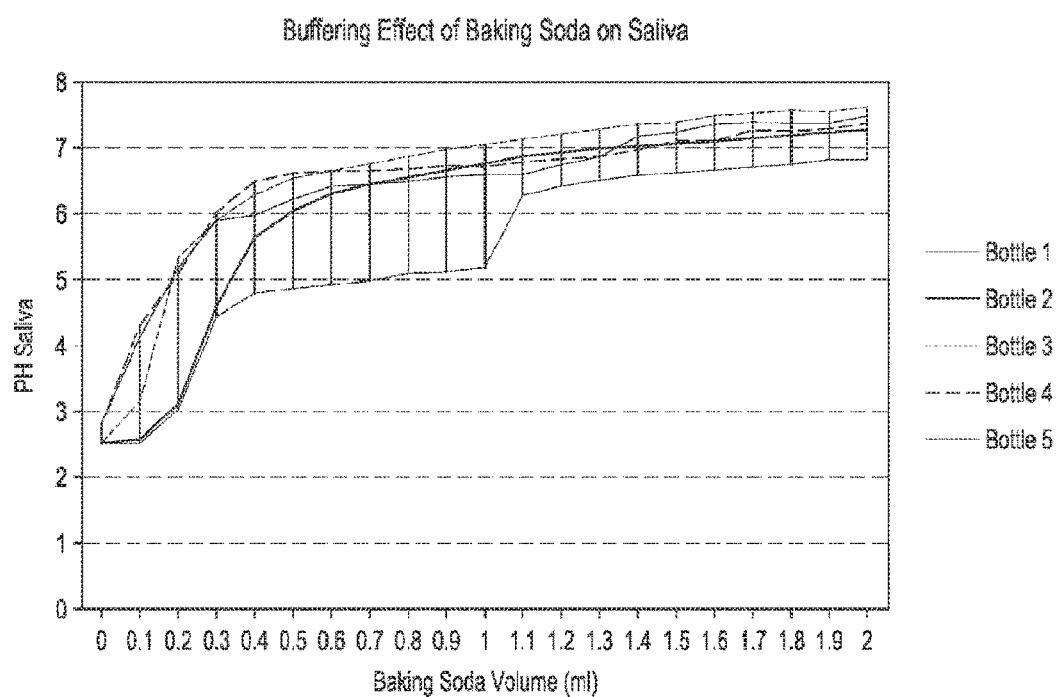
FIG. 3 illustrates the effectiveness of sodium bicarbonate in neutralizing acidic saliva.

FIG. 3 graphically illustrates the effectiveness of sodium bicarbonate in neutralizing the acidic saliva. Table 5 indicates the amount of 3M sodium bicarbonate that is needed to adjust the pH of the saliva from 2.5 to 6.8 or greater.

TABLE 5

Effectiveness of Sodium Bicarbonate in Neutralizing Acidic Saliva

| Volume Baking Soda | pH Sample 1 | pH Sample 2 | pH Sample 3 | pH Sample 4 | pH Sample 5 |
|---|---|---|---|---|---|
| 0.00 | 2.49 | 2.5 | 2.54 | 2.79 | 2.81 |
| 0.10 | 2.52 | 2.56 | 3.14 | 4.32 | 4.15 |
| 0.20 | 3.07 | 3.1 | 5.31 | 5.12 | 5.18 |
| 0.30 | 4.50 | 4.63 | 5.88 | 6.01 | 5.89 |
| 0.40 | 4.80 | 5.66 | 6.28 | 6.48 | 6.01 |
| 0.50 | 4.85 | 6.05 | 6.52 | 6.58 | 6.23 |
| 0.60 | 4.92 | 6.29 | 6.65 | 6.61 | 6.41 |
| 0.70 | 4.98 | 6.45 | 6.75 | 6.65 | 6.44 |
| 0.80 | 5.08 | 6.58 | 6.85 | 6.67 | 6.5 |
| 0.90 | 5.12 | 6.67 | 7.02 | 6.7 | 6.56 |
| 1.00 | 5.19 | 6.77 | 7.06 | 6.72 | 6.57 |
| 1.10 | 6.28 | 6.86 | 7.13 | 6.77 | 6.59 |
| 1.20 | 6.43 | 6.9 | 7.21 | 6.78 | 6.73 |
| 1.30 | 6.53 | 6.96 | 7.27 | 6.86 | 6.89 |
| 1.40 | 6.60 | 7.01 | 7.35 | 6.97 | 7.12 |
| 1.50 | 6.61 | 7.08 | 7.4 | 7.09 | 7.22 |
| 1.60 | 6.64 | 7.11 | 7.49 | 7.13 | 7.35 |
| 1.70 | 6.70 | 7.18 | 7.51 | 7.25 | 7.39 |
| 1.80 | 6.73 | 7.2 | 7.56 | 7.3 | 7.4 |
| 1.90 | 6.80 | 7.27 | 7.58 | 7.35 | 7.41 |
| 2.00 | 6.81 | 7.3 | 7.61 | 7.39 | 7.49 |

Figure 4:
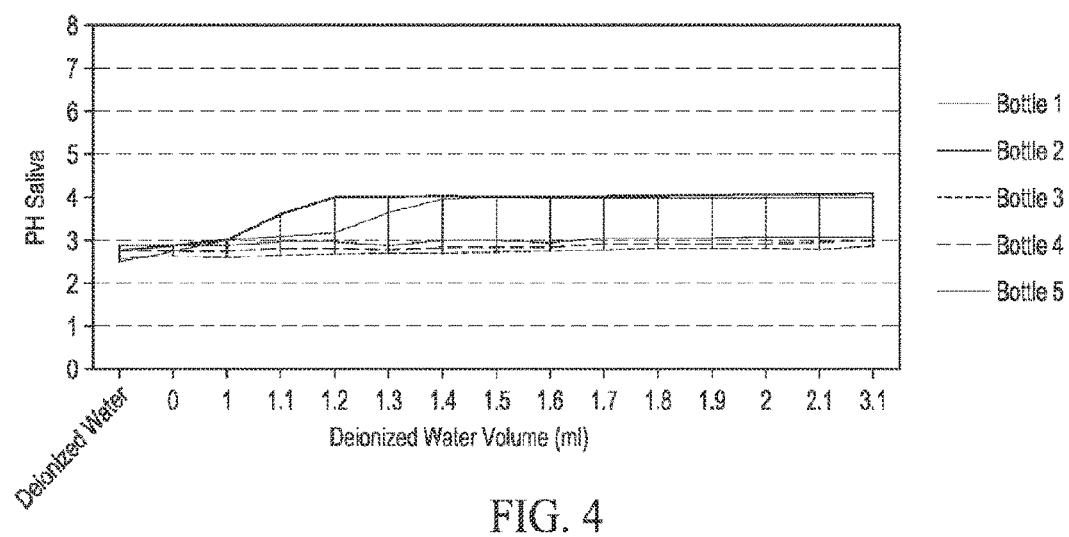
FIG. 4 illustrates the buffering capacity of deionized water on saliva.

FIG. 4 graphically illustrates that water alone is not effective in increasing the pH of the saliva to the neutral pH of 6.5-7, and that the natural buffering effect of saliva is not enough to raise the pH.

These results indicate that acid erosion in the mouth can be prevented and treated by applying an agent capable of neutralizing the acid in the mouth and re-hardening the tooth enamel, and applying an agent capable of re-mineralizing the teeth. Table 6 illustrates the formulation for preventing and treating tooth erosion.

TABLE 6

Formulations for Neutralizing Agent and Re-mineralizing Agent

| Neutralizing Agent (Step 1) | |
|---|---|
| Sodium Bicarbonate | 0.5-5 wt % |
| Calcium phosphate component | |
| Calcium Chloride | 0.01-0.1 wt % |
| Potassium Phosphate | 0.005-0.05% |
| Arginine Bicarbonate | 1-8 wt % |
| Eucalyptus oil | 1 drop |
| Licorice root extract | 1 drop |
| Re-mineralizing Agent (Step 2) | |
| Casein phosphopeptide, amorphous calcium phosphate | 0.1-10 wt % |
| Sodium Fluoride | 0.01-1 wt % |
| Green Tea Extract | 50-400 mg/mL |

Discussion

As can be seen above, only 2.0 mLs of a 3M solution of sodium bicarbonate is needed to neutralize the acidic saliva to a pH of 7.0. We hence decided in order to combat acid erosion in the mouth we needed to approach it from two directions.

First Neutralize the Acid by a Solution Containing:

1. Sodium bicarbonate, shown in our research to buffer and neutralize the acid

2. Eucalyptus oil, flavoring agent 3. 1 to 8% Arginine solution, natural protein present in saliva. It helps in buffering acidic pH.

4. Calcium phosphate, present in artificial saliva. It has been shown to increase microhardness of enamel in our research data.

5. Licorice root extract, acting as a salivary and gustatory stimulant, and a natural antibacterial remedy.

The results of our research shows that rinsing with a sodium bicarbonate solution for 30 seconds is sufficient to help neutralize the saliva; and furthermore eliminate the horrific taste that patients experience as a result of acidic vomitus or acidic regurgitation.

In our experience, patients that experience the horrific taste of acid regurgitation and vomitus are more than willing to use a two step mouth wash, if it can help them eliminate the taste and esophageal burn and discomfort one experiences after throwing up. One of the biggest mistakes patients make after an acidic challenge is to brush their teeth, in order to get rid of the acidic taste of vomitus. Brushing immediately after an acidic regurgitation can be an important factor to further deteriorate enamel as a result of erosion-abrasion caused by the friction and wear between toothbrush bristles incorporating acid into enamel Second Remineralize the Enamel by Rinsing with Solution in Step 2, that Contain the Following Ingredients:

1. CPP-ACP (Casein phosphopeptide, derived from casein protein in milk, and amorphous calcium phosphate).

2. Fluoride, 0.05% NaF (230 ppm)

3. Green Tea Extract, shown to increase microhardness in dentin and enamel, and also have anticarious properties;

Formulation for the Two Step Neutralizing Mouth Wash

Step One: Combination of the Following

1. Baking soda 6.24 g baking soda (equivalent to 1 teaspoon) in 240 ml water (2.6%)

Range: 0.5-5%

2. 1 drop of Eucalyptus oil in 240 ml water 3. 1 to 8% Arginine solution (Arginine Bicarbonate)—4 to 30 grams 4. Calcium phosphate component ('artificial saliva')

1.5 mM $CaCl_2.2H_2O$; Range: 0.5-5 mM 0.9 mM $KH_2PO_4$; Range 0.1-5 mM

5. Licorice root extract

Step Two: Combination of the Following

1. CPP-ACP (Recaldent)

Casein phosphopeptide, derived from casein protein in milk, Amorphous calcium phosphate Range: 0.1-10%

2. Fluoride 0.05% NaF (230 ppm F)

Range: 0.01-1%

3. Green Tea Extract:

Range 50 mg/ml, 100 mg/ml, 200 mg/ml, 300 mg/ml and 400 mg/ml)

Instructions:

Rinse with step one for 30 seconds, spit and rinse with step two for 30 seconds and spit. The patient should not eat or drink for 30 minutes following treatment.

Example 4: Investigation of Treatment Options to Minimize the Effects of Acid Erosion on Enamel Introduction:

Acid erosion of teeth is a significant oral health problem that has become more prevalent in the recent years due to the popularity of diets high in acidic contents, increase in use of medication causing low salivary flow and systemic conditions such as GERD and bulimia. Erosive tooth wear is a form of chemical tooth loss that causes enamel dissolution without involvement of bacterial origin (1). Erosive tooth wear can cause significant tooth damage compromising the esthetics and function of teeth. It no longer affects only the elderly population, and can manifest in all age groups of our society. The earlier dentists diagnose and recommend a preventive regimen for their patients, the more minimal the long lasting effects of tooth erosion.

According to the World Health Organization, dental erosion is the progressive and irreversible loss of hard tissue that is chemically etched away from the tooth surface by extrinsic and/or intrinsic acids by a process that does not involve bacteria. Erosive tooth wear is a significant oral health problem once it compromises the esthetics and function of natural teeth. Chronic health conditions such as gastroesophageal reflux disease (GERD), hiatal hernia, and bulimia nervosa can cause erosive tooth wear from exposure to hydrochloric acid during involuntary regurgitation of stomach juices (2-4). Prevalence of dental erosion in GERD patients was reported to be 24%, 5 and the National Eating Disorder Association has reported approximately 11 million Americans suffer from eating disorders (6).

Softening of the enamel surface is an early manifestation of acid erosion. Subsequently, the tooth structures are dissolved layer by layer or by a mechanical insult, resulting in bulk-loss of tooth material. The majority of dentists can recall seeing a patient in their dental office with moderate to advanced erosion and tooth wear present on the lingual and incisal edges of their upper anterior teeth as a manifestation of a systemic condition such as Bulimia and GERDS. The majority of these patients require extensive restorative work to return the teeth to optimal function and esthetics.

Case Study: A 46 year old female with a history of acid reflux presented in our office, with extensive erosion on the lingual and incisal edges of her maxillary incisors. The patent informed us that she had been suffering from the symptoms of GERDS for years, but had only recently been placed on medication. She complained of sensitivity on her teeth and was dissatisfied with her smile. Initial examination revealed incisal wear and chipping on the incisal edges, and lingual surface of the upper anteriors, and incisal wear and chipping on the lower anterior teeth. Recurrent decay and occlusal erosion was present on the posterior teeth. Abfraction lesions were present on the facial of teeth #4, #5, #6, #11, #12, #13, #14, #19, #20, and #21. Generalized occlusal wear was present on all teeth.

Treatment:

This patient's treatment plan included Empress Veneers on teeth #7& #10, and Empress Crowns on #8 & #9, porcelain fused to metal crowns on teeth #18, #19, #28, #30, and #31. Incisal composite bonding on the lower anteriors, and class V composites on teeth #4, #5, #12, #13, #20, #21, and #29. An occlusal guard was also treatment planned to stabilize and protect the teeth and prevent damage to the teeth and restorations due to bruxism.

Many patients with dental manifestation of GERDS and bulimia may exhibit more severe tooth destruction, requiring extensive and in some cases full mouth rehabilitation. The ideal scenario for a dentist would be to detect the early signs of erosion in their patients and recommend a preventive regimen in order to minimize and maybe prevent the damage to the dentition from chronic acid exposure.

The most significant natural defense in the oral cavity remains to be saliva, which modulates the severity of erosion by diluting, clearing, and neutralizing the acid, and by supplying the necessary calcium and phosphate ions for re-mineralization.[7] This protective role may not always be sufficient as tooth erosion is evident in a significant number of patients. It may take several hours of re-mineralization to achieve the complete rehardening of softened enamel.8 One contributing factor can be further tooth erosion-abrasion resulting from brushing immediately after an acidic regurgitation.

Various products containing fluoride and/or calcium phosphate are readily available for caries prevention. These products should benefit erosion cases via re-mineralization as well. Fluoride, in the presence of calcium and phosphate, shifts the equilibrium surrounding the tooth surface towards re-mineralization. An acidic challenge in a patient suffering from GERDS or bulimia, can cause an undersaturation of salivary salts (calcium, phosphate), which can contribute to the demineralization of tooth structure.[9,10] Delivery of these minerals to the oral environment by self-application through a mouth rinse or tooth cream is a practical approach for patients with acid regurgitation.

Objectives:

This in-vitro study investigated the ability of four treatments to increase the hardening of tooth enamel initially softened by hydrochloric acid, as found in patients with gastric reflux and bulimia. The treatments consisted of products that contain calcium, phosphate, and/or fluoride, and were compared with hardening by saliva alone. Surface microhardness is used to assess enamel softening associated with the initial stage of the erosion process and enamel rehardening to indicate the effectiveness of various preventive treatments.

Materials and Methods

Specimen Preparation: 25 extracted human molars (IRB #10-01122-XM) were cut into buccal and lingual halves and embedded in acrylic resin. The teeth were collected from dental clinics in the region and stored in 10% buffered formalin acetate. Buccal and lingual surfaces were free of caries and congenital defects. The enamel surface was ground to achieve a flat surface ca 5×5 mm, using 240, 400 and 600 grit silicon carbide paper, and polished with 1.0 and 0.05 micron alumina suspension before the baseline surface hardness measurement.

Surface Hardness Measurement:

Enamel surface hardness was measured with a microhardness tester (Micromet™ 2103, Buehler) using a Vickers indenter at 50 g load for 15 s. Four indentations were performed to obtain an average hardness for each specimen.

Hydrochloric Acid Immersion (Softening stage)—The specimens were immersed in 25 ml of 37 degrees C. 10 mM hydrochloric acid pH 2.5 for 10 min to mimic an acid challenge from stomach acid regurgitation. The teeth were collected from dental clinics in the region and stored in 10% buffered formalin acetate. Buccal and lingual surfaces were free of caries and congenital defects. The enamel surface was ground to achieve a flat surface, ca 5×5 mm, using 240, 400 and 600 grit silicon carbide paper, and polished with 1.0 and 0.05 micron alumina suspension before the baseline surface hardness measurement. The specimens were then rinsed with 5 ml tap water to simulate a patient rinsing. Surface hardness of the enamel at 'softening' stage was measured after the specimens were dried with compressed air for 30 sec.

Treatments and Saliva Immersion (Rehardening stage)—Resting saliva was collected from five participants in the morning of each day of the experiment and pooled together (IRB #10-01122-XM). The participants were advised not to brush that morning to avoid the influence of toothpaste. One of the following treatments was applied onto the softened enamel surface: 0.05% Sodium fluoride mouth rinse (ACT, Chattem) for 1 min, 0.4% stannous fluoride gel (Gel-Kam, Colgate Palmolive), casein phosphopeptide amorphous calcium phosphate (CPP-ACP) (Prospec™ MI Paste, GC Corp) for 3 min, fluoridated CPP-ACP paste (MI Paste Plus, GC Corp) for 3 min. Deionized water was used as a control. After the aforementioned contact time according to manufacturer instructions, the treatments were wiped off and the specimens were immersed in 5 ml of pooled saliva and stored in 37 degrees C. incubator. After one hour, the specimens were rinsed with deionized water, dried with compressed air for 30 sec, and the surface hardness was measured ('rehardening stage'). Sample size was 10 per group.

Data Analysis and Statistical Analysis—Percent hardness reduction from the hydrochloric acid challenge and percent hardness recovery after the treatment and saliva immersion were calculated from the differences in Vickers hardness numbers between the baseline, softening, and rehardening stages. The data was analyzed using ANOVA statistics and Student-Newman-Keuls post-hoc test at a significance level of 0.05.

Results

Vickers hardness values of the enamel surface at different stages of the experiment were obtained. No significant difference in baseline microhardness was found among groups ($p>0.05$). The hardness significantly reduced after immersion in hydrochloric acid ($p<0.05$). One-hour immersion in saliva alone did not significantly increase the hardness of softened enamel ($p>0.05$). Treatment with ACT mouth rinse and Gel-Kam followed by one-hour saliva immersion increased the hardness, but it was not significantly different from the hardness at the softening stage ($p>0.05$). Hardness of the specimens treated with MI-Paste and MI-Plus followed by saliva immersion increased significantly compared to the softening stage ($p<0.05$). The hardness values of specimens in the rehardening stage were significantly lower than the baseline hardness values in all groups, except those treated with MI-Plus. Also determined were the percentage of hardness recovery, calculated from the ratio of hardness gain at the rehardening stage and the hardness loss at the softening stage. One-hour immersion in saliva resulted in 16% hardness recovery. Treatment with either fluoride or MI Paste before immersion in saliva improved the hardness recovery to 51-55%. The treatment that combined fluoride and CPP-ACP resulted in a 78% hardness recovery.

Discussion

Preservation of dental hard tissues is at the forefront of dental health care. Considering the implications of tooth erosion associated with chronic health issues like stomach acid regurgitation, prevention is the best service dental professionals can offer to patients. Patients with GERD have been shown to have significantly higher erosive tooth wear than a control group (11). Dental enamel loss caused by tooth brushing abrasion can be minimized by advising patients to avoid brushing their teeth immediately after an acid regurgitation so that saliva can neutralize the acid and remineralize the affected tooth surfaces. However, it is not clear how long a patient should wait, and how much recovery will be achieved even when he/she has normal salivary function.

We chose 10 min immersion in hydrochloric acid pH 2.5 to represent the contact duration of a stomach acid regurgitation episode. This procedure reduced the enamel hardness by approximately 10%, which is similar to the values obtained with a cola drink (12). Within the scope of the current in vitro study, a one-hour immersion in saliva could recover 16% of the hardness loss from the hydrochloric acid challenge. Another in vitro study showed that enamel softened by citric acid could achieve complete rehardening after 6 hours re-mineralization in artificial saliva (8). Others reported 30% and 60% hardness recovery of bovine enamels softened by a cola drink after 1 hour and 48 hours exposure to an intraoral environment (13) whereas another in situ study reported only a 3% increase in post-erosion hardness of human enamel after 2 days (14). Jaeggi and Lussi (15) suggested a waiting period of one hour before tooth brushing after an erosive challenge, which reduced toothbrush abrasion approximately 24%, whereas a half-hour waiting period reduced abrasion 13%. In addition to the inconsistent recovery, such a prolonged waiting time is not practical. Hence a preventive treatment to enhance the saliva ability to reharden softened enamel is desirable.

Softened enamel representing the stage of erosion where a remaining scaffold of mineral crystals can still be remineralized or rehardened (16). Fluoride enhances re-mineralization of early carious lesion by adsorbing onto the partially dissolved crystal lattice, which attracts calcium and phosphate ions to precipitate (17). In vitro and in situ studies have shown that a single or repetitive exposure to fluoride month rinse, fluoride gel, or 5000 ppm fluoride toothpaste, could slow down or prevent the erosive process (18-20). In the present study, both fluoride mouth rinse and fluoride gel recovered approximately 50% of the lost hardness in comparison to 16% in the saliva group. Interestingly, the CPP-ACP group hardness recovery was also in the 50% range. Reynolds et al. (21) reported similar re-mineralization for a toothpaste containing either 2% CPP-ACP or 2800 ppm fluoride in an in situ study.

A systematic review based on clinical in situ trials indicated that CPP-ACP could remineralize initial enamel caries lesions (22). Similar to the present study, several in vitro and in situ studies showed that CPP-ACP paste increased the hardness of enamel softened by acid erosion (12, 14, 23). The addition of fluoride enhanced the re-mineralization potential of CPP-ACP in an initial caries lesion and enamel softened by cola drink (14, 21). In the present study, the percentage of hardness recovery in the fluoridated CPP-ACP group was 78% compared to 51-55% in the fluoride mouth rinse, gel, and CPP-ACP paste groups. In addition, only the fluoridated CPP-ACP group regained hardness at the rehardening stage that was not significantly different from the baseline hardness value. This value was not a complete hardness recovery, but it indicates the potential of preventive treatments to reduce the effect of tooth damage from acid erosion and supports the concept of simultaneous fluoride and calcium phosphate application in re-mineralization.

Preventive treatments that can reduce tooth damage from hydrochloric acid erosion will certainly benefit patients suffering from stomach acid regurgitation due to GERD and eating disorders. Until more effective preventive treatments are developed, practical and available products used after an acid reflux episode may help reduce erosion. The current study evaluated the effectiveness for a wide range of such options. Although this study may be limited by its in vitro nature, we have shown that the results of the investigated preventive treatments were similar to studies that used in situ models. Moreover, since the initial stage of tooth erosion is likely to have common characteristics, the demonstrated effectiveness of various preventive treatments can be expected to also benefit the preventive treatment of erosive tooth wear from other causes.

Conclusion

Our in vitro study showed that after a 10 minutes exposure of enamel in hydrochloric acid pH 2.5, there was a 10% reduction in enamel hardness. One hour immersion in saliva alone was not adequate to significantly increase the hardness recovery of enamel. However the treatment that combined fluoride and CPP-ACP in conjunction with immersion in saliva resulted in the highest hardness recovery. This recovery could be a result of replenishing salivary salts (calcium and phosphate), which are diminished as a result of an acidic challenge and adding the fluoride to help the re-mineralization of softened enamel. The most effective preventive regimens for a patient suffering from GERDS or bulimia should include immediate use of a fluoride and CPP-ACP treatment and avoidance of tooth brushing following an acidic challenge. Further clinical studies are necessary to determine the effectiveness of these products.

Example 5: Double Layer Neutralizing and Re-Mineralizing Lollipop

This example describes the preparation of a double layered lollipop.
Equipment needed: Large metal mold, 250 mL beaker, scoops, stir bar, weigh boat, glass stir rod, and plastic mold.
Ingredients: (excess)
Xylitol (41.246 g, 82.5%)
Crosslinked PVP (Kollidon® Cl) (8.25 g, 16.5%)
Glycerin (0.5 g, 1%, 10 drops)
Large mold: 11.723 g, 11.720 g (Mean=11.7215 g)
Small mold: 4.828 g, 5.123 g (Mean=4.9755 g)
Average outer layer mass: 6.746 g
Instructions:
1. Assemble a large mold and lightly grease the plastic mold by using cooking spray and wiping down until only a residue remains.
2. Weigh 41.25 g of xylitol (82.5%) and place it into a 250 mL beaker.
3. Heat the xylitol at beaker temperature of 150° C. until it is completely clear. Breaking the surface of the xylitol with a glass stir bar may speed up the process by forcing the solid sections to be exposed to heat. When it is mostly melted, adding a stir bar at 200 RPM will further speed up the process.
4. When the xylitol is completely melted, slowly add 8.25 g (16.5%) Kollidon® CL to the beaker to ensure proper mixing. Increase the stir bar to 450 RPM or manually stir with a glass rod to speed up this process.
5. Add 0.5 g (1%, 10 drops) of glycerin.
6. Pour two samples into each mold and allow 24-48 hours to congeal.
7. Weigh the samples and subtract the average mass of the small mold from the average mass of the large mold to determine the average amount of the outer layer that can be poured around the inner core using the provided mold.

Example 6: Inner Core and Outer Layer Preparation

This example describes the preparation of a Multi-layered lollipop having an inner core and an outer layer.
Inner Core Preparation:
Equipment needed:
250 mL beaker, scoops, stir bar, weigh boat, glass stir rod, and plastic mold.
Ingredients:
Xylitol (56.473 g, 80.6%)
Crosslinked PVP Kollidon® Cl (11.2945 g, 16.1%)
Casein Phosphopeptide (1.4 g, 2%)
$CaCl_2$, (0.0308 g, 0.044%)
$KH_2PO_4$ (0.0168 g, 0.024%)

NaF (0.035 g, 0.05%)
Glycerin (0.7 g, 1%, 14 drops)
Green Tea Extract (solid, 0.025 g, 0.036%)
Licorice Extract (solid 0.025 g, 0.036%)
Eucalyptus oil (3 drops)

Instructions for Preparing the Inner Core:

1. Spray a plastic mold with cooking spray, and wipe down so that only a thin layer of oil is coating the mold.

2. In order to make 10 lollipops, weigh the following amounts: Measure 56.473 g of xylitol (80.6%) in a weigh boat and transfer it into a 250 mL beaker.

3. Heat the xylitol at beaker temperature of 150° C. until it is completely clear. Breaking the surface of the xylitol with a glass stir bar to speed up the process and ensure an even heating by forcing the solid sections to be exposed to heat. When mostly melted, add a stir bar at 200 RPM to further speed up the process.

4. When the xylitol is completely melted, slowly add 11.2945 g (16.1%) of Kollidon® CL to the beaker to ensure proper mixing. Increase the stir bar to 450 RPM or manually stir with a glass rod to speed up the process. The mixture should become very thick.

5. Add 0.035 g (0.05%) of NaF to the mixture and ensure an even mixing.

6. Add 0.0168 g (0.024%) of $KH_2PO_4$ to the mixture and ensure even mixing.

7. Quickly measure 0.0308 g (0.044%) of $CaCl_2$ to the mixture and ensure even mixing. The measurement must be done quickly because the ingredient is hygroscopic, and will become sticky somewhat quickly which will make the amount added inaccurate.

8. Add 0.7 g (1%, 14 drops) of glycerin.

9. Add 0.025 g (0.035%) of green tea extract and ensure proper mixing.

10. Add 0.025 g (0.035%) of licorice extract and ensure even mixing.

11. Add three drops of eucalyptus oil. Note that this substance is volatile and produces vapor.

12. Quickly add 1.4 g (2%) of Casein Phosphopeptide and mix into the mixture. Mix manually with glass stir rod in conjunction with the stir bar to ensure an even mixture as quickly as possible.

13 Immediately pour the mixture into the labeled mold and allow it to congeal at room temperature (20° C.) for 24 to 48 hours.

14. Place sticks into the body of the lollipop after several minutes.

Outer Layer Preparation:

Equipment needed:
250 mL beaker, scoops, stir bar, weigh boat, glass stir rod, and plastic mold.

Ingredients:
Xylitol (57.125 g, 81.6%)
Kollidon® Cl (11.425 g, 16.3%)
Glycerin (0.7 g, 1%, 14 drops)
Green Tea Extract (solid, 0.025 g, 0.036%)
Licorice Extract (solid, 0.025 g, 0.036%)
Eucalyptus oil (3 drops)
L-Arginine (0.7 g, 1%)

Instructions for Preparing the Outer Layer:

1. Spray a plastic mold with cooking spray, and wipe down so that only a thin layer of oil is coating the mold.

2. In order to make 10 lollipops, we need to weigh the following amounts

3. Measure 57.125 g of xylitol (81.6%) in a weigh boat and transfer it into a 250 mL beaker.

4. Heat the xylitol at beaker temperature at 150° C. until completely clear. Breaking the surface of the xylitol with a glass stir bar may speed up the process by forcing the solid sections to be exposed to heat. When mostly melted, adding a stir bar at 200 RPM will further speed up the process.

5. When the xylitol is completely melted, slowly add 11.425 g (16.3%) of Kollidon® Cl to the beaker to ensure proper mixing. Increasing the stir bar to 450 RPM or manually stirring with a glass rod may speed up this process.

6. Add 0.7 g (1%, 14 drops) of glycerin.

7. Add 0.025 g (0.035%) of green tea extract and ensure proper mixing.

8. Add 0.025 g (0.035%) of licorice extract and ensure even mixing.

9. Add three drops of eucalyptus oil. Note that this substance is volatile and produces vapor.

10. Quickly add 0.7 g (1%) of arginine and mix into the mixture. Mix manually with a glass stir rod in conjunction with a stir bar to ensure an even mixture as quickly as possible.

11 Immediately pour mixture into the labeled mold and allow the mixture to congeal at room temperature (20° C.) for 24 to 48 hours.

Example 7: pH Experiment Procedure

Figure 15:
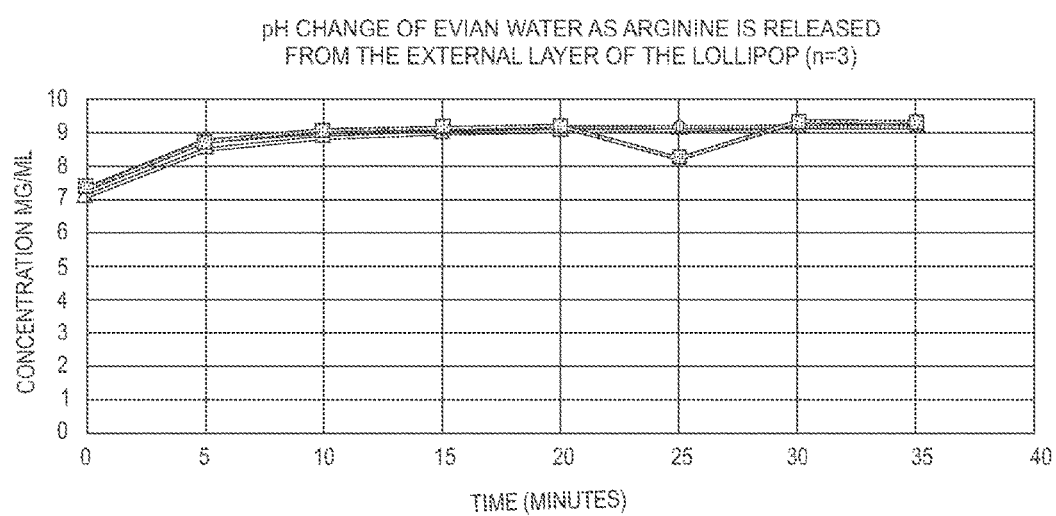
FIG. 15 illustrates pH change of water (e.g., Evian® water) as arginine is released from an external layer of a lollipop over a period of time (e.g., minutes) with n=3.

This experiment was performed on the sample lollipops made in Example 6. This experiment studied the pH change of water (e.g., Evian® water) when arginine was released in the presence of the other ingredients from an outer layer of the lollipop, and the results are shown in FIG. 15. Different pH standards were used for standardizing the pH meter only.

Equipment needed:
Stopwatch, pH meter, pH standard solutions (4, 7, 10), mass scale, samples to be tested, 100 mL beaker, DIW, stir bar, graph for data.

Instructions:

1. Pour 60 mL of deionized water into a 100 mL beaker with a stir bar, and set aside.

2. Calibrate the pH electrode meter according to instrument-specific instructions, using 4.0, 7.0 and 10.0 standard solutions, and store the electrode in a 7.0 storage solution.

3. Set stir plate speed to 250 RPM.

4. Insert the pH probe into the beaker with the deionized water.

5. When ready, simultaneously add a lollipop sample to the stirring solution and start the stop watch.

6. Immediately take a first reading for $T_0$.

7. Continue taking measurements every 5 minutes until completely dissolved which will be approximately 30 minutes.

8. Record the time at which the sample completely dissolves.

9. Repeat as necessary for the desired number of samples.

As shown in FIG. 15, results showed that from 0 to 5 minutes, the pH of the water increased from about 7.1-7.3 to about 8.7-8.9 as arginine was released from the outer layer of the lollipop. At minutes 10 to 20, the pH steadily stayed at 9, and from 20 to 35 minutes, the pH only dropped for one solution at minute 25 and then the solution went back up to about 9.

Example 8: Ion Preparation Procedure/Release of Calcium and Fluoride

Ion Preparation:
Add the formulation on top of the preparation.

Equipment needed:
250 mL beaker, scoops, stir bar, weigh boat, glass stir rod, and plastic mold.

Figure 13:
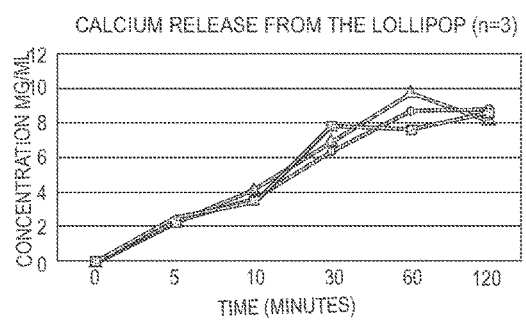
FIG. 13 illustrates calcium release from a lollipop over a period of time (e.g., minutes) with n=3.
Figure 14:
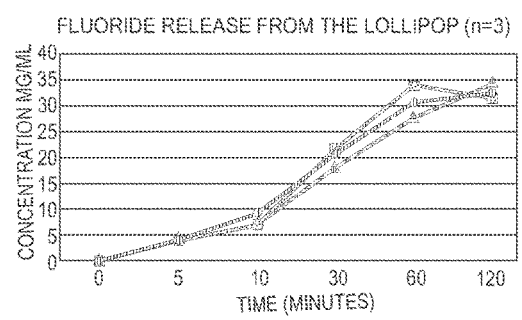
FIG. 14 illustrates fluoride release from a lollipop over a period of time (e.g., minutes) with n=3.

Ingredients:
Xylitol (56.8061 g, 81.1%)
Kollidon® Cl (11.3620 g, 16.2%)
$CaCl_2$ (0.0308 g, 0.044%)
$KH_2PO_4$ (0.0168 g, 0.024%)
NaF (0.035 g, 0.05%)
Glycerin (0.7 g, 1%, 14 drops)
Instructions:
1. Measure 56.8061 g of xylitol (81.1%) in a weigh boat and pour into a 250 mL beaker.
2. Heat the xylitol at beaker temperature at 150° C. until completely clear. Breaking the surface of the xylitol with a glass stir bar may speed up process by forcing the solid sections to be exposed to heat. When mostly melted, adding a stir bar at 200 RPM will further speed up the process.
3. When the xylitol is completely melted, slowly add 11.3620 g (16.2%) of Kollidon® CL to the beaker to ensure proper mixing. Increasing the stir bar to 450 RPM or manually stirring with a glass rod may speed up this process.
4. Add 0.035 g (0.05%) of NaF to the mixture and ensure an even mixing.
5. Add 0.0168 g (0.024%) of $KH_2PO_4$ to the mixture and ensure even mixing.
6. Quickly measure 0.0308 g (0.044%) of $CaCl_2$ to the mixture and ensure even mixing. The measurement must be done quickly because the ingredient is hygroscopic, and will become sticky quickly which will make the amount added inaccurate.
7. Add 1.75 g (2.5%, 30 drops) of glycerin.
8. After ensuring an even mixture, pour the mixture into the labeled mold and allow the mixture to congeal at room temperature (20° C.) for 24 to 48 hours.
Assemblage of 2-stage product:
Equipment needed:
Large metal mold, 250 mL beaker, scoops, stir bar, weigh boat, glass stir rod, and plastic mold.
Ingredients:
Xylitol, Kollidon® Cl, casein phosphopeptide, CaCl2, KH2PO4, NaF, glycerin, green tea extract (solid), licorice extract (solid), eucalyptus oil, arginine.
Instructions:
1. Prepare inner core samples according to the protocol, and let set for 24-48 hours.
2. After congealed, transfer samples to the large metal mold.
3. Prepare the outer layer according to the protocol, adjusted for ½ of all ingredients and pour into the large metal mold over the inner core samples.
4. Place the covering on the metal mold and allowing it to congeal for 24-48 hours.
Release of Calcium and Fluoride:
Release of the calcium and fluoride components of the lollipop were studied, and the results are shown in FIGS. 13 and 14. Steps similar to steps 5-9 of Example 7 above were performed to the sample lollipops except that measurements were taken every 5 minutes up 120 minutes.
As shown in FIGS. 13 and 14, results showed that as time increased, release of the calcium (FIG. 13) and the fluoride (FIG. 14) increased. The highest calcium concentration of about 9.8 mg/ml was recorded at 60 minutes and the highest fluoride concentration of about 34 mg/ml was recorded at about 120 minutes.

Example 9

Lollipop Rehardening Testing:
This example describes a lollipop rehardening test performed on enamel specimens.

Figure 7:
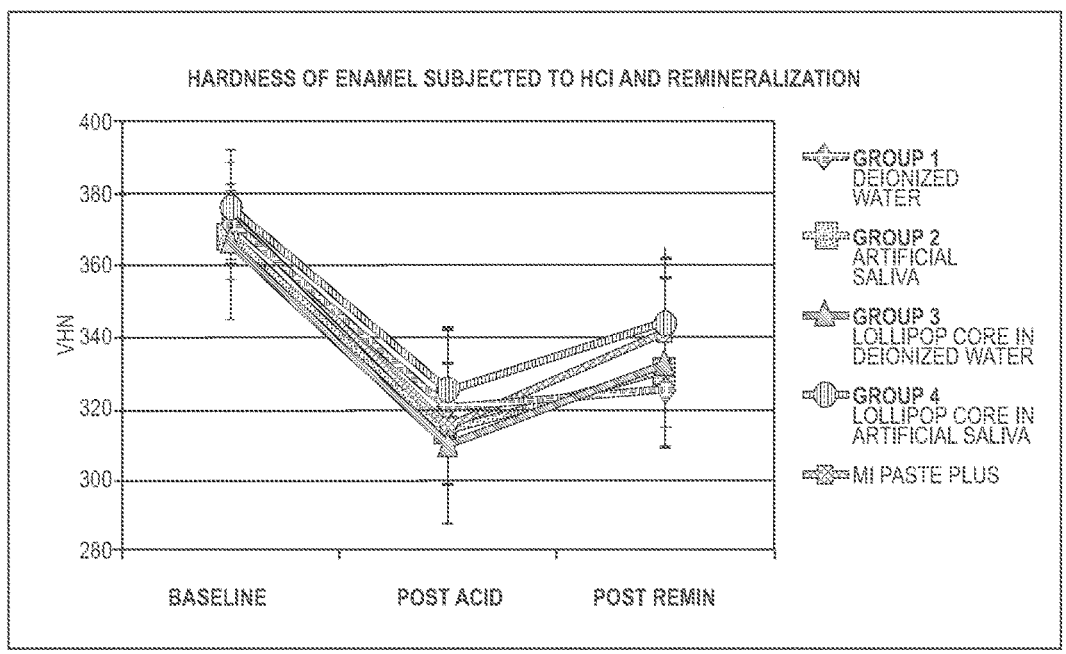
FIG. 7 illustrates the surface hardness of enamel subjected to hydrochloric acid and various formulations of remineralization.
Figure 8:
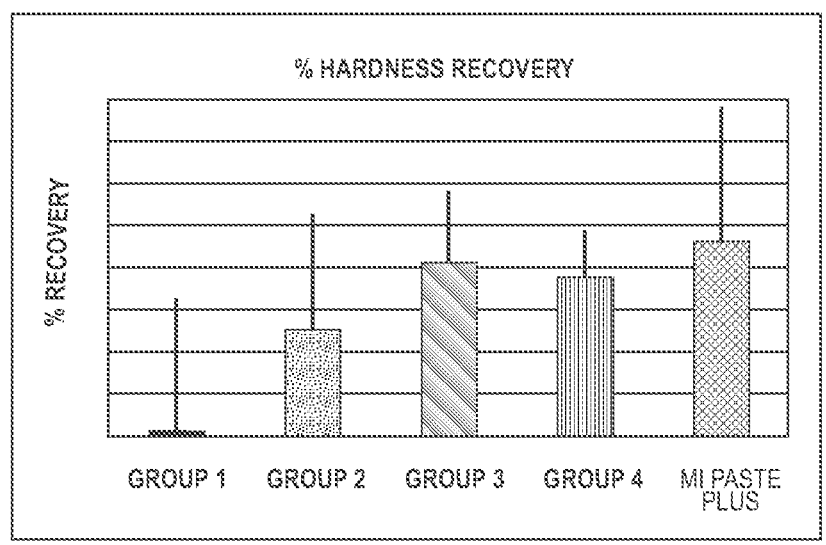
FIG. 8 illustrates the percentage of hardness recovery for enamel subjected to hydrochloric acid and remineralization.

Enamel specimens were cut from buccal and lingual surfaces of extracted human molars (IRB 16-05016-NHSR). Specimens were embedded in acrylic resin and serially polished to obtain flat and smooth surface.
Experimental Steps:
Surface hardness of enamel was measured (Vickers indentor at 200 g load) at a Baseline, after 10 minutes of immersion in 10 mM HCl (post acid), and after one hour immersion in treatment solution (post remineralization).
Treatment Groups (Ten Enamel Samples Per Group):
Group 1 Negative Control A:
One hour immersion in deionized water. This is comparable to a patient with little or no saliva.
Group 2 Negative Control B:
One hour immersion in artificial saliva. This is comparable to a healthy person with normal saliva.
Group 3 Lollipop Core A:
One hour immersion in a lollipop core dissolved in 60 ml deionized water. This is comparable to a patient using a lollipop who has little or no saliva or saliva without ions.
Group 4 Lollipop Core B:
One hour immersion in a lollipop core dissolved in 60 ml of artificial saliva. This is comparable to a patient with normal saliva using a lollipop.
Positive Control:
Three minute application of MI Paste Plus followed by one hour immersion in artificial saliva.
Results:
Table 7 and FIGS. 7 and 8 show Vickers hardness number (VHN) of the baseline, post acid, and post remineralization stages, and percentage recovery (=percentage of hardness gain/hardness loss from softening).

TABLE 7

Percentage Recovery: Hardness Gained and Hardness Lost from Softening Tooth Enamel

| | Baseline | Post acid | Post remin | % recovery |
|---|---|---|---|---|
| Group 1 deionized water | 372 ± 11 | 321 ± 22 | 325 ± 16 | 0.7 ± 32.0 |
| Group 2 artificial saliva | 368 ± 13 | 314 ± 14 | 330 ± 15 | 25.2 ± 27.4 |
| Group 3 lollipop core in deionized water | 367 ± 22 | 310 ± 22 | 333 ± 24 | 41.2 ± 16.9 |
| Group 4 lollipop core in artificial saliva | 376 ± 16 | 325 ± 16 | 344 ± 18 | 37.6 ± 11.4 |
| MI Paste Plus | 375 ± 17 | 316 ± 8 | 342 ± 24 | 46.0 ± 32.3 |

The lollipop core rehardened the softened enamel about 40% (Groups 3 and 4), similar to the MI Paste Plus, a commercial product with many supporting data to prevent/control dental caries, as shown in FIGS. 7 and 8.
Without any treatment, the softened enamel could not reharden as seen in Group 1, the negative control. Artificial saliva rehardened the softened enamel about 25% in Group 2. These negative control groups confirm the reliability of the experimental procedure. Remineralization experiments usually have a high standard deviation, as shown below.

Example 10: Acid Neutralization of Double-Layer Lollipop

This example tested the speed at which a double-layer lollipop would neutralize acid, as well as if neutralized acid could soften enamel.
Procedure (1 Double-Layer Lollipop Per Group; 4 Enamel Samples Per Group)
Part 1:
Dissolve the double-layer lollipop in 40 mL of 10 mM HCL, measure pH every 5 minutes for 20 minutes and used the neutralized acid to softened enamel specimens the same way as in the rehardening study. The same protocol was used for baseline and post acid hardness measurement.

Part 2:

Dissolve the double-layer lollipop in 20 mL of 10 mM HCL, measure pH at 1 minute and use the neutralized acid to softened enamel specimens the same way as in the rehardening study. Also use the same protocol for baseline and post acid hardness measurement.

Results

Table 8 shows pH over time and VHN of the baseline and Post acid stages.

TABLE 8 pH Over Time and VHN of the Baseline and Post Acid Stages.

| | | Time (minutes) | | | | |
|---|---|---|---|---|---|---|
| | | 0 | 5 | 10 | 15 | 20 |
| pH Part 1 | pH | 2.7 | 8.8 | 9.2 | 9.4 | 9.5 |

| | | Time (minutes) | |
|---|---|---|---|
| | | 0 | 1 |
| pH Part 2 | pH | 2.8 | 7.9 |

| | VHN | Baseline | Post acid |
|---|---|---|---|
| Hardness | Part 1 | 370 ± 13 | 373 ± 18 |
| | Part 2 | 383 ± 7 | 384 ± 4 |

Summary of Findings

The double-layer lollipop neutralized acid very fast. pH of HCl increased to above 7 in 1 minute and continued to increase at least 20 minutes. The neutralized acid, as fast as 1 minute contact with the double-layer lollipop, did not soften enamel.

Figure 11:
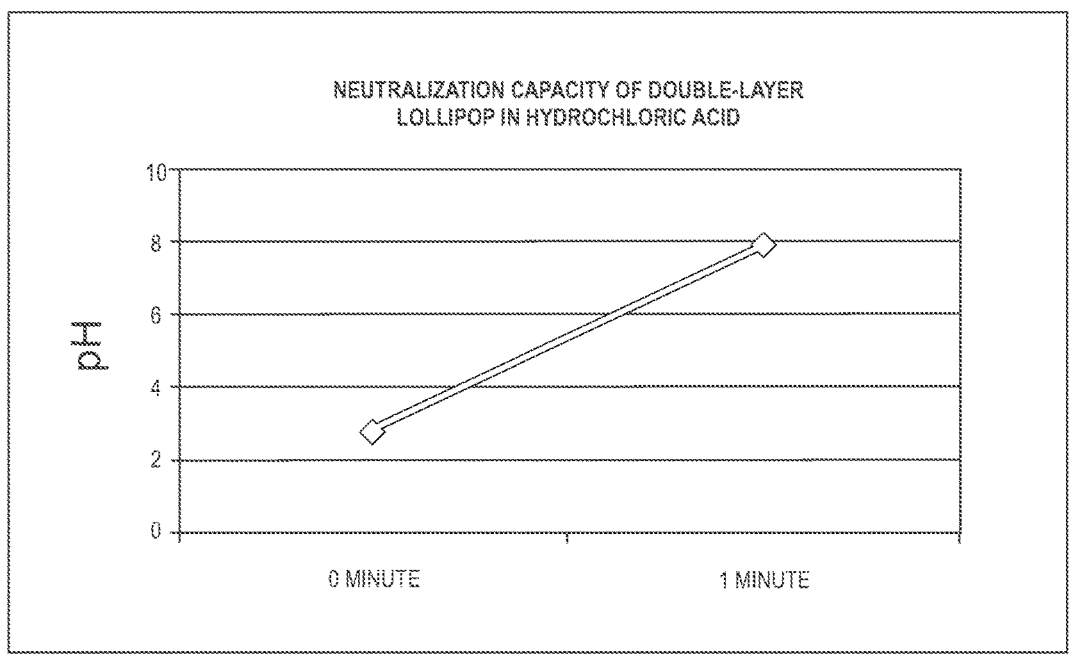
FIG. 11 illustrates the neutralization capacity of a multi-layer (e.g., double-layer) lollipop subjected to hydrochloric acid over a period of one minute.
Figure 12:
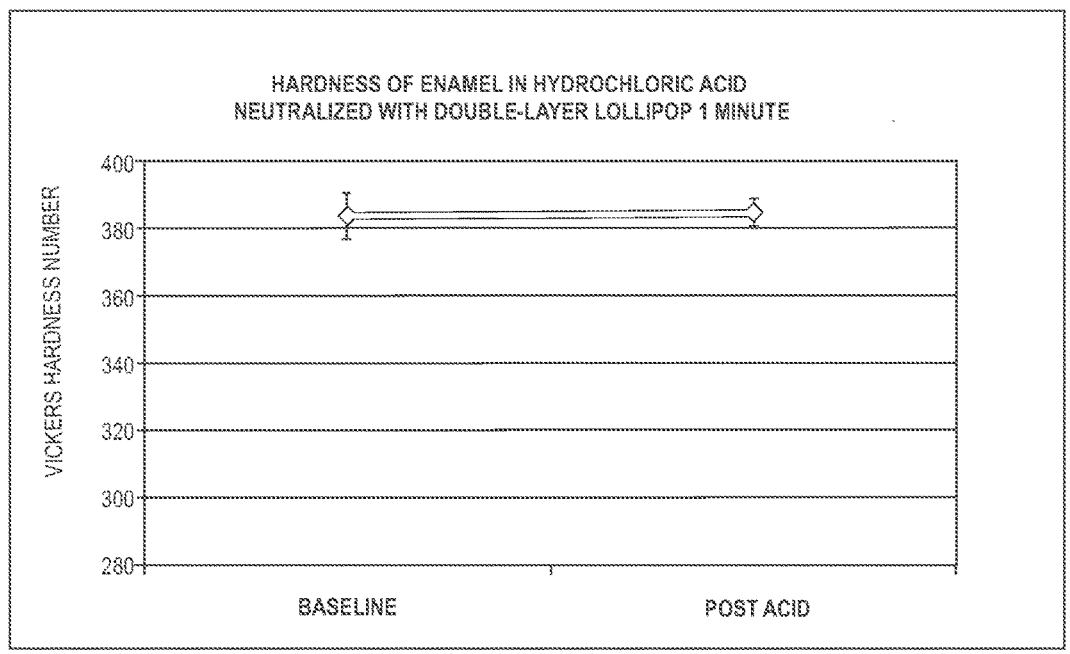
FIG. 12 illustrates the hardness of enamel when subjected to hydrochloric acid and then neutralized with a multi-layer (e.g., double-layer) lollipop for a period of one minute.

FIG. 11 reflects the results of the part 2 neutralization study. These results were unexpected as the lollipop neutralized the HCL faster than expected (e.g., in one minute). FIG. 12 reflects the results of the part 2 hardness study.

Example 11: Rehardening with Lollipop Core at Double Concentration

This example tested if more rehardening effect would result when the lollipop concentration is higher. This scenario is comparable to a patient with a low salivary flow rate.

Procedure (6 Enamel Samples Per Group)

The same protocol as the rehardening experiment was used, except the lollipop core was dissolved in 30 ml of deionized water or artificial saliva.

Results

Figure 9:
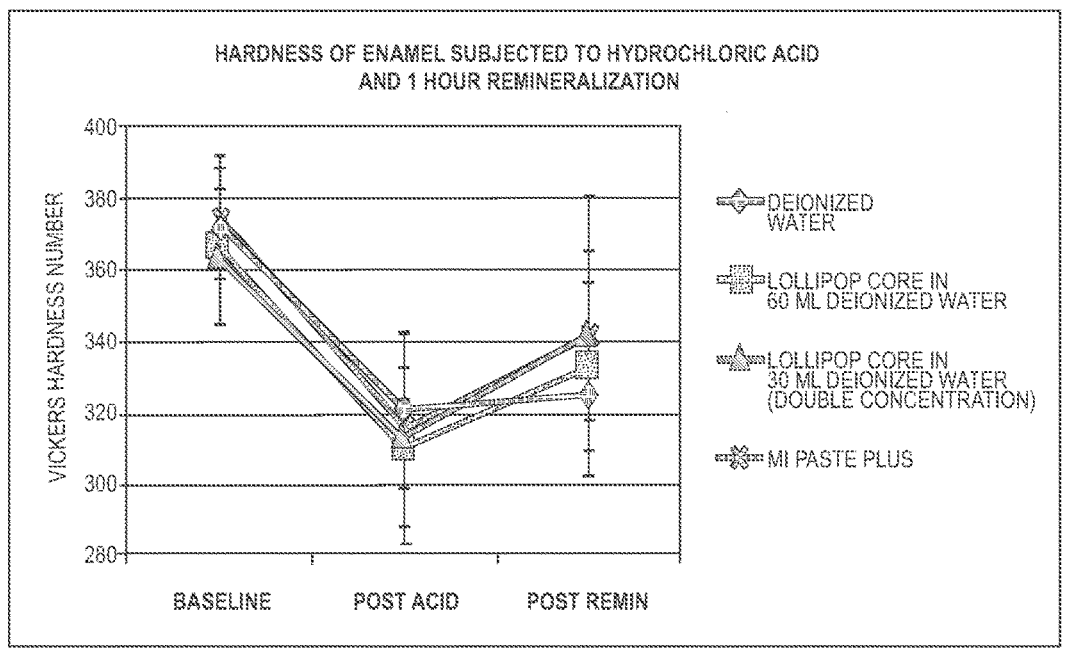
FIG. 9 illustrates the surface hardness of enamel subjected to hydrochloric acid and remineralization in a scenario of lower salivary flow (e.g., to simulate patients with dry mouth) which increased the concentration of the formulation.
Figure 10:
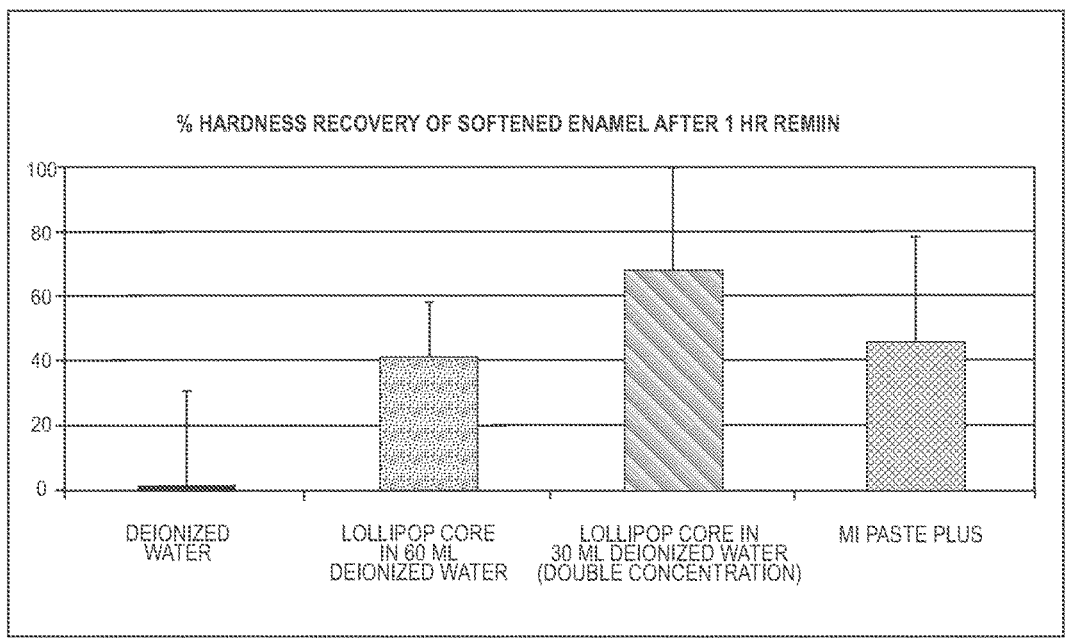
FIG. 10 illustrates the percentage of hardness recovery of softened enamel after remineralization in a scenario of lower salivary flow (e.g., to simulate patients with dry mouth) which increased the concentration of the formulation.

Tables 9 to 11 and FIGS. 9 & 10 show VHN of the baseline, post acid, and post remineralization stages, and % recovery (=percentage of hardness gain/hardness loss from softening).

TABLE 9

Hardness changes: Baseline, Post Acid, Post Remineralization, and Standard Deviation.

| | Hardness changes | | | | | |
|---|---|---|---|---|---|---|
| | Baseline | Post acid | Post Remin | SD | SD | SD |
| Deionized water | 372.2 | 320.7 | 325.2 | 10.6 | 21.9 | 15.7 |
| Lollipop core in 60 ml | 366.9 | 310.2 | 332.8 | 22.0 | 22.4 | 23.7 |
| Lollipop core in 30 ml | 363.8 | 312.7 | 341.7 | 19.3 | 29.7 | 39.2 |
| MI Paste Plus | 374.9 | 315.6 | 341.6 | 17.3 | 8.2 | 23.7 |

FIG. 9 corresponds to Table 9.

TABLE 10

Percentage of Hardness Recovery of Softened Enamel after 1 Hour of Remineralization

| Treatment | % Recovery | SD |
|---|---|---|
| Deionized water | 0.7 | 32.0 |
| Lollipop core in 60 ml deior | 41.2 | 16.9 |
| Lollipop core in 30 ml deior | 68.0 | 43.7 |
| MI Paste Plus | 46.0 | 32.3 |

FIG. 10 corresponds to Table 10.

TABLE 11

VHN of the Baseline, Post acid, and Post Re-mineralizing Stages, and Percent Recovery (=percentage of hardness gain/hardness loss from softening).

| | Baseline | Post acid | Post remin | % recovery |
|---|---|---|---|---|
| Lollipop core in 30 ml deionized water | 364 ± 19 | 313 ± 30 | 342 ± 39 | 68.0 ± 43.7 |
| Lollipop core in 30 ml artificial saliva | 376 ± 11 | 325 ± 10 | 350 ± 11 | 46.5 ± 19.9 |

Summary of Findings

A double concentration of the lollipop core increased rehardening effect, up to 68% when dissolved in deionized water. The rehardening seemed to be less when dissolved in artificial saliva. The same behavior was found in Example 9 which could be considered a random process from variability of the samples.

It is to be understood that any of the Examples described above performed in-vitro are done to mimic in-vivo studies.

REFERENCES

1. Imfeld T. Dental erosion. Definition, classification and links. Eur J Oral Sci 1996; 104:151-155.
2. Schroeder P L, Filler S J, Ramirez B, Lazarchik D A, Vaezi M F, Richter J E. Dental erosion and acid reflux disease. Ann Intern Med 1995; 122:809-815.
3. Valena V, Young W G. Dental erosion patterns from intrinsic acid regurgitation and vomiting. Aust Dent J 2002; 47:106-115.
4. Barron R P, Carmichael R P, Marcon M A, Sandor G K. Dental erosion in gastroesophageal reflux disease. J Can Dent Assoc 2003; 69:84-89.

5. Pace F, Pallotta S, Tonini M, Vakil N, Bianchi Porro G. Systematic review: gastro-oesophageal reflux disease and dental lesions. Aliment Pharm Ther 2008; 27:1179-1186.
6. National Eating Disorders Association. Statistics: Eating disorders and their precursors. http://www.nationaleatingdisorders.org/uploads/statistics_tmp.pdf. Downloaded Nov. 5, 2012.
7. Zero D T, Lussi A. Erosion—chemical and biological factor of importance to the dental practitioner. Int Dent J 2005; 55:285-290.
8. Eisenburger M, Addy M, Hughes J A, Shellis R P. Effect of time on the remineralisation of enamel by synthetic saliva after citric acid erosion. Caries Res 2001; 35:211-215.
9. Scheutzel P. Etiology of dental erosion—intrinsic factors. Eur J Oral Sci 1996; 104:178-190.
10. Jarvinen V K, Rytomaa I I, Heinonen O P. Risk factors in dental erosion. J Dent Res 1991; 70:942-947.
11. Tantbirojn D, Pintado M R, Versluis A, Dunn C, DeLong R. Quantitative analysis of tooth surface loss associated with gastroesophageal reflux disease: A longitudinal clinical study. J Am Dent Assoc 2012; 143:278-285.
12. Panich M, Poolthong S. The effect of casein phosphopeptide-amorphous calcium phosphate and a cola soft drink on in vitro enamel hardness. J Am Dent Assoc 2009; 140:455-460.
13. Kim J W, Jang K T, Lee S H, Kim C C, Hahn S H, Garcia-Godoy F. In vivo rehardening of enamel eroded by a cola drink. ASDC J Dent Child 2001; 68:122-124
14. Srinivasan N, Kavitha M, Loganathan S C. Comparison of the re-mineralization potential of CPP-ACP and CPP-ACP with 900 ppm fluoride on eroded human enamel: An in situ study. Arch Oral Biol 2010; 55:541-544.
15. Jaeggi T, Lussi A. Toothbrush abrasion of erosively altered enamel after intraoral exposure to saliva: an in situ study. Caries Res 1999; 33:455-461.
16. Amaechi, B T, Higham S M. Dental erosion: possible approaches to prevention and control. J Dent 2005; 33:243-252.
17. Featherstone J D C. The Science and Practice of Caries Prevention. J Am Dent Assoc 2000; 131:887-899.
18. Ganss C, Klimek J, Brune V, Schürmann A Effects of two fluoridation measures on erosion progression in human enamel and dentine in situ. Caries Res 2004; 38:561-566.
19. White A J, Jones S B, Barbour M E, Churchley D R, Gracia L H, Rees G D. Inhibition of erosive dissolution by sodium fluoride: Evidence for a dose-response. J Dent 2012; 40:654-660.
20. Ren Y F, Liu X, Fadel N, Malmstrom H, Barnes V, Xu T. Preventive effects of dentifrice containing 5000 ppm fluoride against dental erosion in situ. J Dent 2011; 39:672-678.
21. Reynolds E C, Cai F, Cochrane N J, Shen P, Walker G D, Morgan M V, Reynolds C. Fluoride and casein phosphopeptide-amorphous calcium phosphate. J Dent Res 2008; 87:344-348.
22. Yengopal V, Mickenautsch S. Caries preventive effect of casein phosphopeptide-amorphous calcium phosphate (CPP-ACP): a meta-analysis. Acta Odontol Scand 2009; 67:321-332.
23. Tantbirojn D, Huang A, Ericson M D, Poolthong S. Change in surface hardness of enamel by a cola drink and a CPP-ACP paste. J Dent 2008; 36:74-79.
24. World Health Organization. Dental Diseases and Oral Health. Available at: http://www.who.int/oral_health/publications/en/orh_fact_sheet.pdf. Accessed Apr. 17, 2014.
25. National Eating Disorders Association. Get the Facts on Eating Disorders. http://www.nationaleatingdisorders.org/get-facts-eating-disorders. Accessed Apr. 17, 2013.

Publications by Investigators in Scientific Journals Related to this Disclosure

1. Dehghan M, Ozorio J E V, Chanin S, Tantbirojn D, Versluis A, Garcia-Godoy F. Investigating enamel loss when brushing with an anti-erosive toothpaste after an acidic episode. Accepted for publication General Dentistry 2016.
2. Dehghan M, Tantbirojn D, Kymer-Davis E, Stewart C W, Zhang Y H, Versluis A, García-Godoy F. Neutralizing saliva pH by mouthwashes after an acidic challenge. Journal of Investigative and Clinical Dentistry, November 30 doi: 10.1111/jicd.12198.
3. Fitzhugh A C, Dehghan M, Tantbirojn D, Simon, Effectiveness of a Neutralizing Mouthwash in rehardening Softened Enamel. Journal Cosmetic Dentistry 2014:30(3) Fall:72-79, 2014.
4. Dehghan M, Stanely P J, Tantbirojn D, Versluis A. "Investigation of Treatment Options to Minimize The effects of Acid Erosion on Enamel." Gen Dent 2014 July/August; 62(4): e30-e33.
5. Dehghan M, Alex Fitzhugh, Tantbirojn D, Versluis A. "Hardness Recovery of Softened Enamel after Neutralizing and Fluoride rinse". J Dent Research 2013; 91 (Spec Issue): Abstract 174900
6. Dehghan M, Stanley P J, Tantbijorn D, Versluis A. Investigation of Treatments to Improve Hardness Recovery of Softened Enamel. J Dent Research 2012; 91 (Spec Issue): Abstract 330.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An oral composition, the oral composition comprising crosslinked polyvinylpyrrolidone (PVP) and xylitol, and the xylitol and crosslinked PVP are in a ratio of about 5:1, wherein the oral composition is in the form of a lozenge or lollipop.

2. The oral composition according to claim 1, wherein the composition further comprises glycerin, L-arginine, sodium fluoride, monopotassium phosphate, calcium chloride, green tea extract, licorice extract, eucalyptus oil, and casein phosphopeptide.

3. An oral composition according to claim 1 for neutralizing saliva and re-hardening tooth enamel, the oral composition comprising an alkalinizing agent; a re-mineralizing agent; a base; a plasticizer; and a sugar alcohol, wherein the oral composition is in the form of a lozenge or a lollipop.

4. The composition according to claim 3, wherein the base comprises crosslinked polyvinylpyrrolidone (PVP), the plasticizer comprises glycerin, and the sugar alcohol comprises xylitol.

5. The composition according to claim 4, wherein the crosslinked PVP is in an amount of from about 5 to about 50% of the composition, the xylitol is in an amount of from about 20 to about 95% of the composition, and the glycerin is in an amount of from about 0.1 to about 1% of the composition.

6. The composition according to claim 3, wherein the alkalinizing agent comprises (i) a re-hardening agent, (ii) eucalyptus, (iii) licorice root, and (iv) arginine.

7. The composition according to claim 6, wherein the alkalinizing agent comprises sodium bicarbonate, or potassium bicarbonate, and the re-hardening agent comprises calcium chloride, potassium phosphate and/or casein phosphopeptide.

8. The composition according to claim 3, wherein the re-mineralizing agent comprises calcium chloride, monopotassium phosphate, and/or sodium fluoride.

9. The composition according to claim 8, wherein the calcium chloride is in an amount of from about 0.01 to about 0.5% of the composition, the monopotassium phosphate is in an amount of from about 0.01 to about 0.5% of the composition, and/or the sodium fluoride is in an amount of from about 0.01 to about 0.1% of the composition.

10. The composition according to claim 4, wherein the composition is administered to a user's teeth via the lollipop or lozenge carrier for a time of from about 1 to about 20 minutes.

11. The composition according to claim 10, wherein the composition raises the user's saliva pH from about 7 to about 10.

12. The composition according to claim 3, wherein the composition further comprises green tea extract.

13. A multi-layer lozenge or lollipop for neutralizing saliva and re-hardening tooth enamel, the lozenge or lollipop comprising an alkalinizing agent; a re-mineralizing agent; a base comprising crosslinked polyvinylpyrrolidone (PVP); a plasticizer; and a sugar alcohol comprising xylitol, wherein the xylitol and crosslinked PVP are in a 5:1 ratio, and wherein the lozenge or lollipop upon oral administration raises the saliva pH from about 7 to about 10 in about 1 minute.

14. The multi-layer lozenge or lollipop according to claim 13, wherein the lozenge or lollipop further comprises an inner core and an outer layer, and the lollipop upon oral administration is dissolved within about 20 minutes.

15. The multi-layer lozenge or lollipop according to claim 13, wherein the plasticizer comprises glycerin.

16. The multi-layer lozenge or lollipop according to claim 15, wherein the crosslinked PVP is in an amount of from about 5 to about 50% of the lozenge or lollipop, the xylitol is in an amount of from about 20 to about 95% of the lozenge or lollipop, and the glycerin is in an amount of from about 0.1 to about 1% of the lozenge or lollipop.

17. The multi-layer lozenge or lollipop according to claim 13, wherein the alkalinizing agent comprises (i) a re-hardening agent, (ii) eucalyptus, (iii) licorice root, and (iv) L-arginine.

18. The multi-layer lozenge or lollipop according to claim 17, wherein the alkalinizing agent comprises sodium bicarbonate, or potassium bicarbonate, and the re-hardening agent comprises calcium chloride, potassium phosphate or casein phosphopeptide.

19. The multi-layer lozenge or lollipop according to claim 13, wherein (i) the re-mineralizing agent comprises calcium chloride, monopotassium phosphate, and/or sodium fluoride; and (ii) the lozenge or lollipop further comprises green tea extract.

20. The multi-layer lozenge or lollipop according to claim 19, wherein the calcium chloride is in an amount of from about 0.01 to about 0.5% of the lozenge or lollipop, the monopotassium phosphate is in an amount of from about 0.01 to about 0.5% of the lozenge or lollipop, and/or the sodium fluoride is in an amount of from about 0.01 to about 0.1% of the lozenge or lollipop.

21. A method of making a multi-layer lozenge or lollipop for neutralizing saliva and re-hardening tooth enamel, the method comprising: molding an inner core, the inner core comprising, xylitol, crosslinked polyvinylpyrrolidone (PVP), and glycerin; and molding an outer layer over the inner core, the outer layer comprising xylitol, crosslinked PVP, glycerin, and L-arginine.

22. The method according to claim 21, wherein the inner core further comprises sodium fluoride, monopotassium phosphate, calcium chloride, green tea extract, licorice extract, eucalyptus oil, and casein phosphopeptide; and the outer layer further comprises green tea extract, licorice extract, and eucalyptus oil.

23. The method according to claim 21, wherein molding the inner core further comprises congealing the inner core in a mold for a period of time, and then inserting a stick into a portion of the inner core, and after the inserting of the stick into a portion of the inner core, the outer layer is then molded over the inner core.

* * * * *